United States Patent [19]

Bundy et al.

[11] Patent Number: 5,795,986
[45] Date of Patent: Aug. 18, 1998

[54] PYRIMIDO|4,5-B|INDOLES

[75] Inventors: Gordon L. Bundy, Portage; John R. Palmer, Kalamazoo, both of Mich.

[73] Assignee: Pharmacia & Upjohn Company, Kalamazoo, Mich.

[21] Appl. No.: 875,466
[22] PCT Filed: Mar. 1, 1996
[86] PCT No.: PCT/US96/02397
§ 371 Date: Jul. 25, 1997
§ 102(e) Date: Jul. 25, 1997
[87] PCT Pub. No.: WO96/26941
PCT Pub. Date: Sep. 6, 1996

Related U.S. Application Data

[63] Continuation-in-part of Ser. No. 398,201, Mar. 2, 1995, abandoned.
[51] Int. Cl.[6] .................................. C07D 487/04
[52] U.S. Cl. .................................. 544/115; 544/250
[58] Field of Search .................................. 544/115, 250

[56]  References Cited

PUBLICATIONS

WO93/20078 (Oct. 1993).

*Primary Examiner*—Robert W. Ramsuer
*Attorney, Agent, or Firm*—Bruce Stein

[57]  ABSTRACT

The pyrimido|4,5-b|indoles (I)

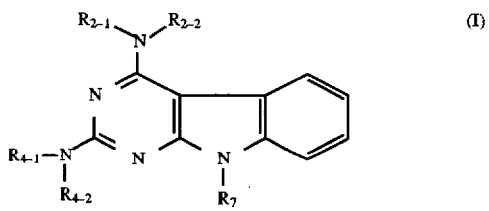

and lactams (XIII) of the invention are useful as pharmaceutical agents for a number of different indications.

12 Claims, No Drawings

PYRIMIDO[4,5-B]INDOLES

This application is a continuation (national phase) of International Application No. PCT/US96/02397, International Filing Date 1 Mar. 1996, which was a continuation-in-part of U.S. patent application Ser. No. 08/398,201 filed 2 Mar. 1995, now abandoned.

BACKGROUND OF THE INVENTION

1. Field of the Invention

The pyrimido[4,5-b]indoles (I) and the lactams (XIII) of the invention are useful as pharmaceutical agents for a number of different indications.

2. Description of the Related Art

The pyrimido[4,5-b]indoles (I) and the lactams (XIII) of the present invention are chemically structurally similar to pyrrolo[2,3-d]pyrimidines.

International Publication No. WO93/20078 discloses both pyrrolo[2,3-d]) pyrimidines and pyrimido[4,5-b]indoles. In WO93/20078, the bicyclic heterocyclic amines (XXX) are actually tricyclic when $R_5$ and $R_6$ are taken together with the attached carbon atom to form a ring. The compounds of the present invention are a selection invention of International Publication No. WO93/20078.

GB 1,268,772 discloses tricyclic compounds where the diaminosubstituted ring is not a pyrimidinyl ring system.

*J. Heterocyclic. Chem.*, 25, 1633–39 (1988) discloses compounds which have various oxygenated groups attached to the six membered non-pyrimidinyl ring. The compounds of the present invention do not have any oxygen functionality on the six member non-pyrimidinyl ring.

SUMMARY OF INVENTION

Disclosed are pyrimido[4,5-b]indoles of the formula (I)

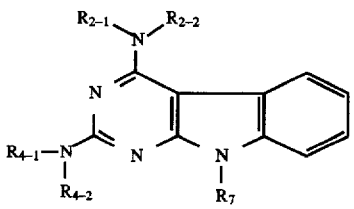

where $R_{2-1}$ is (A) —H, (B) $C_1$–$C_8$ alkyl optionally substituted with 1 thru 4
- (1) —F,
- (2) —Cl,
- (3) —OR$_{2-10}$ where R$_{2-10}$ is
  - (a) —H,
  - (b) $C_1$–$C_4$ alkyl,
  - (c) phosphate,
  - (d) sulfate,
  - (e) —CO—R$_{2-11}$ where R$_{2-11}$ is $C_1$–$C_4$ alkyl or $C_6$–$C_9$ aralkyl,
  - (f) —CO—NR$_{2-12}$R$_{2-13}$ where R$_{2-12}$ and R$_{2-13}$ are the same or different and are —H or $C_1$–$C_3$ alkyl,
  - (g) sulfamate,
  - (h) glucosyl,
  - (i) galactosyl,
  - (j) glucuronic acid,
  - (k) maltosyl,
  - (l) arabinosyl,
  - (m) xylosyl,
  - (n) —CO—CH(NH$_2$) —H,
  - (o) —CO—CH(NH$_2$) —CH$_3$,
  - (p) —CO—CH(NH$_2$) —CH(CH$_3$)$_2$,
  - (q) —CO—CH(NH$_2$) —CH$_2$—CH(CH$_3$)$_2$,
  - (r) —CO—CH(NH$_2$) —CH(CH$_3$) —CH$_2$—CH$_3$,
  - (s) —CO—CH(NH$_2$) —CH$_2$—OH,
  - (t) —CO—CH(NH$_2$) —CH(OH)—CH$_3$,
  - (u) —CO—CH(NH$_2$) —CH$_2$—φ,
  - (v) —CO—CH(NH$_2$) —CH$_2$—|p-phenyl|—OH,
  - (w) —CO—CH(NH$_2$) —CH$_2$|2-indolyl|
  - (x) —CO—CH(NH$_2$) —CH$_2$—SH,
  - (y) —CO—CH(NH$_2$) —CH$_2$—CH$_2$—S—CH$_3$,
  - (z) —CO—C*H—NH—CH$_2$—CH$_2$—C*H$_2$ where the carbon atoms marked with an "*" are bonded together to form a heterocyclic ring,
  - (aa) —CO—C*H—NH—CH$_2$—CH(OH)—C*H$_2$ where the carbon atoms marked with an "*" are bonded together to form a heterocyclic ring,
  - (bb) —CO—CH(NH$_2$) —CH$_2$—COOH,
  - (cc) —CO—CH(NH$_2$) —CH$_2$—CONH$_2$,
  - (dd) —CO—CH(NH$_2$) —CH$_2$—CH$_2$—COOH,
  - (ee) —CO—CH(NH$_2$) —CH$_2$—CH$_2$—CONH$_2$,
  - (ff) —CO—CH(NH$_2$) —CH$_2$—C*—NH—CH=N—C*H= where the carbon atoms marked with an "*" are bonded together to form a heterocyclic ring,
  - (gg) —CO—CH(NH$_2$) —CH$_2$—CH$_2$—CH$_2$—NH—C(=NH)—NH$_2$,
  - (hh) —CO—CH(NH$_2$) —CH$_2$—CH$_2$—CH$_2$—CH$_2$—NH$_2$
  - (ii) —CO—CH(NH$_2$) —CH$_2$—CH$_2$—CH(OH)—CH$_2$—NH$_2$,
  - (jj) —CO—CH$_2$—CH$_2$—NH$_2$,
  - (kk) —CO—CH$_2$—CH$_2$—CH$_2$—NH$_2$,
  - (ll) —CO—CH(NH$_2$) —CH$_2$—CH$_2$—CH$_2$—NH$_2$,
  - (mm) —CO—CH(NH$_2$) —CH$_2$—CH$_2$—CH$_2$—NH—CO—NH$_2$,
  - (nn) —CO—CH(NH$_2$) —CH$_2$—CH$_2$—OH,
- (4) —N(R$_{2-14}$)$_2$ where R$_{2-14}$ may be the same or different and is
  - (a) $C_1$–$C_6$ alkyl optionally substituted with 1 thru 3 —OH or —OCH$_3$,
  - (b) $C_1$–$C_6$ alkylcarbonyl,
  - (c) $C_1$–$C_6$ alkoxycarbonyl,
  - (d) $C_6$–$C_{12}$ arylalkyl,
  - (e) —φ,
  - (f) —SO$_2$—$C_1$–$C_8$ alkyl,
  - (g) CH$_3$—C*—O—CO—O—C*—CH$_2$— where the carbon atoms marked by an asterisk (*) are attached by a double bond to form a five member ring, where $R_{2-2}$ is (A) —H, (B) $C_1$–$C_8$ alkyl optionally substituted with 1 thru 4
- (1) —F,
- (2) —Cl,
- (3) —OR$_{2-10}$ where R$_{2-10}$ is as defined above,
- (4) —N(R$_{2-14}$)$_2$ where R$_{2-14}$ may be the same or different and is as defined above, or R$_{2-1}$ and R$_{2-2}$ are taken together with the attached nitrogen atom to form a heterocyclic ring selected from the group consisting of (A) 1-pyrrolidinyl optionally substituted on carbon with 1 thru 3 R$_{2-3}$ where R$_{2-3}$ is selected from the group of
- (1) $C_1$–$C_6$ alkyl optionally substituted with 1 thru 3 —OH or —OCH$_3$,
- (2) $C_1$–$C_6$ alkenyl optionally substituted with 1 thru 3 —OH or —OCH$_3$, (3) $C_1$–$C_6$ alkylcarbonyl,
(4) $C_1$–$C_6$ alkoxycarbonyl,
(5) $C_6$–$C_{12}$ arylalkyl,
(6) =O,
(7) —OH,
(8) —C≡N,
(9) —CO $_2R_{2-4}$ where $R_{2-4}$ is
 (a) —H,
 (b) $C_1$–$C_4$ alkyl,
 (c) $C_6$–$C_{12}$ aryl,
 (d) $C_6$–$C_{12}$ aralkyl,
(10) —$NH_2$,
(11) —Cl,
(12) —F,
(13) —Br,
(14) —φ optionally substituted with 1 thru 3 —F, —Cl, —Br, —OH, —$OCH_3$, —$OCH_2$—φ, —$NO_2$, $C_1$–$C_3$ alkyl, —$NH_2$, –$NHCH_3$, $N(CH_3)_2$, —CO $_2R_{2-4}$ is as defined above,
(15) —$(CH_2)_{n4}NR_{2-6}R_{2-7}$ where $R_{2-6}$ and $R_{2-7}$ are the same or different and are $C_1$–$C_4$ alkyl or may taken together with the attached nitrogen atom to form the heterocyclic ring —N*—$(CH_2)_{n5}$—$R_{2-8}$—$(CH_2)_{n6}$* where the atoms marked with an asterisk (*) are bonded together resulting in the formation of a ring, where $n_4$ is 0 thru 3, $n_5$ is 1 thru 5, $n_6$ is 0 thru 3 and $R_{2-8}$ is
 (a) —$CH_2$—,
 (b) —O—,
 (c) —S—,
 (d) —N $R_{2-4}$ where $R_{2-4}$ is as defined above, (B) 1-piperdinyl optionally substituted on carbon with 1 thru 3 $R_{2-3}$ where $R_{2-3}$ is as defined above, (C) 1-morpholinyl optionally substituted on carbon with 1 thru 3 $R_{2-3}$ where $R_{2-3}$ is as defined above, (D) 1-piperazinyl optionally substituted on carbon with 1 thru 3 $R_{2-3}$ where $R_{2-3}$ is as defined above and optionally substituted in the 4-position with $R_{2-5}$ where $R_{2-5}$ is
 (1) $C_1$–$C_6$ alkyl optionally substituted with 1 thru 3—OH or —$OCH_3$,
 (2) $C_1$–$C_6$ alkylcarbonyl,
 (3) $C_1$–$C_6$ alkoxycarbonyl,
 (4) $C_6$–$C_{12}$ arylalkyl,
 (5) —φ,
 (6) —$SO_2$–$C_1$–$C_8$ alkyl,
 (7) $CH_3$–C*—O—CO—O—C*—$CH_2$-where the carbon atoms marked by an asterisk (*) are attached by a double bond to form a five member ring, (E) 1-aziridinyl optionally substituted on carbon with 1 thru 2 $R_{2-3}$ where $R_{2-3}$ is as defined above, (F) 1-azetidinyl optionally substituted on carbon with 1 thru 3 $R_2$, where $R_{2-3}$ is as defined above, (G) 1-hexamethyleneimino optionally substituted on carbon with 1 thru 3 $R_{2\ 3}$ where $R_{2\ 3}$ is as defined above, (H) 1-pyrrolyl optionally substituted on carbon with 1 thru 3 $R_{2-3}$ where $R_{2\ 3}$ is as defined above, (I) 1-imidazolyl optionally substituted on carbon with 1 thru 3 $R_{2-3}$, where $R_{2-3}$ is as defined above, (J) 1-pyrazoyl optionally substituted on carbon with 1 thru 3 $R_{2-3}$ where $R_{2-3}$ is as defined above, (K) 1-pyrazolidinyl optionally substituted on carbon with 1 thru 3 $R_{2-3}$ where $R_{2-3}$ is as defined above, (L) 1, 2, 3-triazolyl optionally substituted on carbon with 1 thru 3 $R_{2-3}$ where $R_{2-3}$ is as defined above.

(M) 1, 2, 4-triazolyl optionally substituted on carbon with 1 thru 3 $R_{2-3}$ where $R_{2-3}$ is as defined above, (N) 1-tetrazolyl optionally substituted on carbon with 1 thru 3 $R_{2-3}$ where $R_{2-3}$ is as defined above, (O) 1-thiomorpholinyl optionally substituted on carbon with 1 thru 3 $R_{2-3}$ where $R_{2-3}$ is as defined above, (P) 1-thiazolidinyl, optionally substituted on carbon with 1 thru 3 $R_{2-3}$ where $R_{2-3}$ is as defined above, (Q) ($R_{2-1}/R_{2-2}$-1)

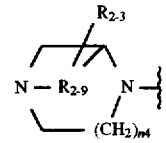

(R) ($R_{2-1}/R_{2-2}$-2)

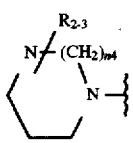

(S) ($R_{2-1}/R_{2-2}$-3)

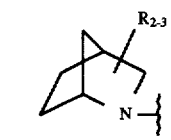

(T) ($R_{2-1}/R_{2-2}$-4)

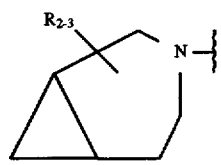

(U) ($R_{2-1}/R_{2-2}$-5)

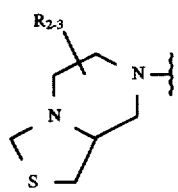

(V) ($R_{2-1}/R_{2-2}$-6)

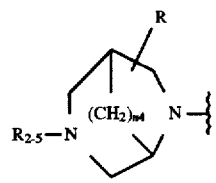

(W) ($R_{2-1}/R_{2-2}$-7)

-continued

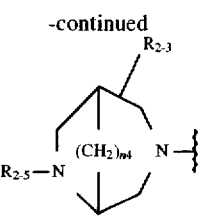

(X) ($R_{2-1}/R_{2-2}$-8)

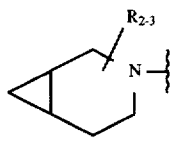

(Y) ($R_{2-1}/R_{2-2}$-9)

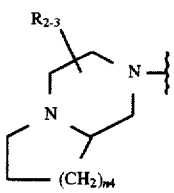

(Z) ($R_{2-1}/R_{2-2}$-10)

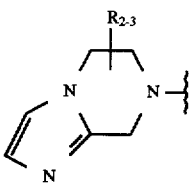

(AA) ($R_{2-1}/R_{2-2}$-11)

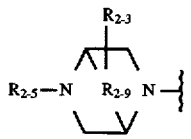

(BB) ($R_{2-1}/R_{2-2}$-12)

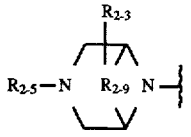

(CC) ($R_{2-1}/R_{2-2}$-13)

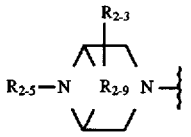

where $R_{2-3}$ and $R_{2-5}$ are as defined above.
where $R_{2-9}$ is
(A) —$(CH_2)_{n4}$ where $n_4$ is 1 thru 3,
(B) —$CH_2OCH_2$—
(C) —$CH_2SCH_2$—
(D) —$CH_2SO_2CH_2$—
(E) —$CH_2SO$—
(F) —$CH_2SO_2$—
(G) —$CH_2N(R_{2-5})CH_2$— where $R_{2-5}$ is as defined above.

where $R_{4-1}$ is defined the same as $R_{2-1}$, but may be the same or different than $R_{2-1}$,
where $R_{4-2}$ is defined the same as $R_{2-2}$, but may be the same or different than $R_{2-2}$;
where $R_7$ is ($C_7$-2)
(B) $C_1$–$C_8$ alkyl substituted with 1 thru 4 $R_{7-1}$ where $R_{7-1}$ is
  (1) —F, —Cl, —Br,
  (2) $C_1$–$C_4$ alkyl,
  (3) —$CF_3$,
  (4) —φ,
  (5) —$OR_{7-2}$ where $R_{7-2}$ is
    (a) —H,
    (b) $C_1$–$C_4$ alkyl,
    (c) phosphate,
    (d) sulfate,
    (e) —CO—$R_{7-8}$ where $R_{7-8}$ is $C_1$–$C_4$ alkyl or $C_6$–$C_9$ aralkyl,
    (f) —CO—$NR_{7-10}R_{7-11}$ where $R_{7-10}$ and $R_{7-11}$ are the same or different and are —H or $C_1$–$C_3$ alkyl,
    (g) sulfamate,
    (h) glucosyl,
    (i) galactosyl,
    (j) glucuronic acid,
    (k) maltosyl,
    (l) arabinosyl,
    (m) xylosyl,
    (n) —CO—CH($NH_2$) —H,
    (o) —CO—CH($NH_2$) —$CH_3$,
    (p) —CO—CH($NH_2$) —CH($CH_3$)$_2$,
    (q) —CO—CH($NH_2$) —$CH_2$—CH($CH_3$)$_2$,
    (r) —CO—CH($NH_2$) —CH($CH_3$) —$CH_2$—$CH_3$,
    (s) —CO—CH($NH_2$) —$CH_2$—OH
    (t) —CO—CH($NH_2$) —CH(OH)—$CH_3$,
    (u) —CO—CH($NH_2$) —$CH_2$—φ,
    (v) —CO—CH($NH_2$) —$CH_2$—[p-phenyl]—OH,
    (w) —CO—CH($NH_2$) —$CH_2$—[2-indolyl]
    (x) —CO—CH($NH_2$) —$CH_2$—$CH_2$—SH,
    (y) —CO—CH($NH_2$) —$CH_2$—$CH_2$—S—$CH_3$,
    (z) —CO—C*H—NH—$CH_2$—$CH_2$-C *$H_2$ where the carbon atoms marked with an asterisk (*) are bonded together to form a heterocyclic ring,
    (aa) —CO—C H—NH—$CH_2$—CH(OH)—C*$H_2$ where the carbon atoms marked with an asterisk (*) are bonded together to form a heterocyclic ring,
    (bb) —CO—CH($NH_2$) —$CH_2$—COOH,
    (cc) —CO—CH($NH_2$) —$CH_2$—CO $NH_2$,
    (dd) —CO—CH($NH_2$) —$CH_2$—$CH_2$—COOH,
    (ee) —CO—CH($NH_2$) —$CH_2$—$CH_2$—CO $NH_2$,
    (ff) —CO—CH($NH_2$) —$CH_2$—C*—NH—CH=— N—C*H= where the carbon atoms marked with an asterisk (*) are bonded together to form a heterocyclic ring,
    (gg) —CO—CH($NH_2$) —$CH_2$—$CH_2$—$CH_2$—NH—C(=NH)—$NH_2$,
    (hh) —CO—CH($NH_2$) —$CH_2$—$CH_2$—$CH_2$—$CH_2$—$NH_2$,
    (ii) —CO—CH($NH_2$) —$CH_2$—$CH_2$—CH(OH)—$CH_2$—$NH_2$,
    (jj) —CO—$CH_2$—$CH_2$—$NH_2$,
    (kk) —CO—$CH_2$—$CH_2$—$CH_2$—$NH_2$,
    (ll) —CO—CH($NH_2$) —$CH_2$—$CH_2$—$CH_2$—$NH_2$,
    (mm) —CO—CH($NH_2$) —$CH_2$—$CH_2$—$CH_2$—NH—CO—$NH_2$,
    (nn) —CO—CH($NH_2$) —$CH_2$—$CH_2$—OH,
  (6) —$SR_{7-2}$ where $R_{7-2}$ is defined above, (7) —NHR$_{7-3}$ where R$_{7-3}$ is —H or C$_1$-C$_4$ alkyl.
(8) —N R$_{7-4}$R$_{7-5}$ where R$_{7-4}$ and R$_{7-5}$ are the same or different and are C$_1$-C$_4$ alkyl or may taken together with the attached nitrogen atom to form the heterocyclic ring —N *—(CH$_2$)$_{n1}$—R$_{5-6}$—(CH$_2$)$_{n2}$* where the atoms marked with an asterisk (*) are bonded together resulting in the formation of a ring. where n$_1$ is 1 thru 5, n$_2$ is 0 thru 3 and R$_{5-6}$ is
(a)—CH$_2$—.
(b)—O—.
(c)—S—.
(d)—N R$_{7-9}$ where R$_{7-9}$ is
  (i) C$_1$-C$_6$ alkyl optionally substituted with 1 thru 3 —OH or —OCH$_3$.
  (ii) C$_1$-C$_6$ alkylcarbonyl.
  (iii) C$_1$-C$_6$ alkoxycarbonyl.
  (iv) C$_6$-C$_{12}$ arylalkyl.
  (v)—φ.
  (vi)—SO$_2$—C$_1$-C$_8$ alkyl.
  (vii) CH$_3$—C*—O—CO—C*—CH$_2$— where the carbon atoms designated by * are attached by a double bond to form a five member ring.
(9) —(CH$_2$)$_{n3}$CO$_2$R$_{7-2}$, where n$_3$ is 0 thru 6 and R$_{7-2}$ is as defined above.
(10) —(CH$_2$)$_{n3}$CON(R$_{7-3}$)$_2$ where $_{n3}$ is as defined as above and where R$_{7-3}$ may be the same or different and is defined above.
(11) —(CH$_2$)$_{n3}$CONR$_{7-4}$R$_{7-5}$ where n$_3$, R$_{7-4}$, R$_{7\,5}$ are as defined above.
(12) —(CH$_2$)$_{n1}$OR$_{7-2}$ where R$_{7-2}$ and n$_1$ are as defined above.
(13) —(CH$_2$)$_{n1}$OCOR$_{7-3}$ where R$_{7-2}$ and n$_1$ are as defined above.
(14) —(CH$_2$)$_{n1}$SR$_{7-2}$ where R$_{7-2}$ and n$_1$ are as defined above.
(15) —(CH$_2$)$_{n1}$NHR$_{7-3}$ where R$_{7-3}$ and n$_1$ are as defined above.
(16) —(CH$_2$)$_{n1}$NR$_{7-4}$R$_{7-5}$ where R$_{7-4}$, R$_{7-5}$, and n$_1$ are as defined above.
(D)—(CH$_2$)$_{n3}$-pyridin-2-, 3- or 4-yl optionally substituted with 1 thru 4 R$_{7-1}$ where n$_3$ and R$_{7-1}$ are as defined above.
(C$_5$-5) (F)—(CH$_2$)$_{n3}$CO$_2$R$_{7-2}$ where n$_3$ and R$_{7-2}$ are as defined above.
(C$_5$-6) (G)—(CH$_2$)$_{n3}$CON(R$_{7-3}$)$_2$ where n$_3$ is as defined as above and where R$_{7-3}$ may be the same or different and is as defined above.
(C$_5$-7) (H)—(CH$_2$)$_{n3}$CONR$_{7-4}$R$_{7-5}$ where n$_3$, R$_{7-4}$, R$_{7-5}$ are as defined above.
(C$_5$-8) (I)—(CH$_2$)$_{n3}$SO$_3$R$_{7-2}$ where n$_3$ and R$_{7-2}$ are as defined above; and pharmaceutically acceptable salts thereof.

Disclosed are lactams of the formula (XIIII)

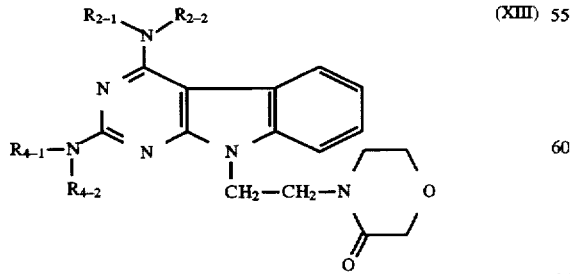

(XIII)

where R$_{2-1}$ is
(A)—H.

(B) C$_1$-C$_8$ alkyl optionally substituted with 1 thru 4
 (1) —F.
 (2) —Cl.
 (3) —OR$_{2-10}$ where R$_{2-10}$ is
  (a)—H.
  (b) C$_1$-C$_4$ alkyl.
  (c) phosphate.
  (d) sulfate.
  (e)—CO—R$_{2-11}$ where R$_{2-11}$ is C$_1$-C$_4$ alkyl or C$_6$-C$_9$ aralkyl.
  (f)—CO—NR$_{2-12}$R$_{2-13}$ where R$_{2-12}$ and R$_{2-13}$ are the same or different and are —H or C$_1$-C$_3$ alkyl.
  (g) sulfamate.
  (h) glucosyl.
  (i) galactosyl.
  (j) glucuronic acid.
  (k) maltosyl.
  (l) arabinosyl.
  (m) xylosyl.
  (n)—CO—CH(NH$_2$) —H.
  (o)—CO—CH(NH$_2$) —CH$_3$.
  (p)—CO—CH(NH$_2$) —CH(CH$_3$)$_2$.
  (q)—CO—CH(NH$_2$) —CH$_2$—CH(CH3)$_2$.
  (r)—CO—CH(NH$_2$) —CH(CH$_3$) —CH$_2$—CH$_3$.
  (s)—CO—CH(NH$_2$) —CH$_2$—OH
  (t)—CO—CH(NH$_2$) —CH(OH)—CH$_3$.
  (u)—CO—CH(NH$_2$) —CH$_2$—φ.
  (v)—CO—CH(NH$_2$) —CH$_2$—[p-phenyl]—OH.
  (w)—CO—CH(NH$_2$) —CH$_2$—[2-indolyl]
  (x)—CO—CH(NH$_2$) —CH$_2$—SH.
  (y)—CO—CH(NH$_2$) —CH$_2$—CH$_2$-S—CH$_3$.
  (z)—CO—C*H—NH—CH$_2$—CH$_2$-C*H$_2$ where the carbon atoms marked with an "*" are bonded together to form a heterocyclic ring.
  (aa)—CO—C*H—NH—CH$_2$—CH(OH)—C*H$_2$ where the carbon atoms marked with an "*" are bonded together to form a heterocyclic ring.
  (bb)—CO—CH(NH$_2$) —CH$_2$—COOH.
  (cc)—CO—CH(NH$_2$) —CH$_2$—CO NH$_2$.
  (dd)—CO—CH(NH$_2$) —CH$_2$—CH$_2$—COOH.
  (ee)—CO—CH(NH$_2$) —CH$_2$—CH$_2$—CO NH$_2$.
  (ff)—CO—CH(NH2) —CH$_2$-C*—NH—CH=N—C*H=where the carbon atoms marked with an "*" are bonded together to form a heterocyclic ring.
  (gg)—CO—CH(NH$_2$) —CH$_2$—CH$_2$—CH$_2$—NH—C(=NH)—NH$_2$.
  (hh)—CO—CH(NH$_2$) —CH$_2$—CH$_2$—CH$_2$CH$_2$—NH$_2$.
  (ii)—CO—CH(NH$_2$) —CH$_2$—CH$_2$—CH(OH)—CH$_2$—NH$_2$.
  (jj)—CO—CH$_2$—CH$_2$—NH$_2$.
  (kk)—CO—CH$_2$—CH$_2$—CH$_2$—NH$_2$.
  (ll)—CO—CH(NH$_2$) —CH$_2$—CH$_2$—CH$_2$—NH$_2$.
  (mm)—CO—CH(NH$_2$) —CH$_2$—CH$_2$—CH$_2$—NH—CO—NH$_2$.
  (nn)—CO—CH(NH$_2$) —CH$_2$—CH$_2$—OH.
 (4) —N (R$_{2-14}$)$_2$ where R$_{2-14}$ may be the same or different and is
  (a) C$_1$-C$_6$ alkyl optionally substituted with 1 thru 3—OH or —OCH$_3$.
  (b) C$_1$-C$_6$ alkylcarbonyl.
  (c) C$_1$-C$_6$ alkoxycarbonyl.
  (d) C$_6$-C$_{12}$arylalkyl.
  (e)—φ.
  (f)—SO$_2$-C$_1$-C$_8$ alkyl.
  (g) CH$_3$—C*—O—CO—O—C *—CH$_2$ where the carbon atoms marked by an asterisk (*) are attached by a double bond to form a five member ring.

where $R_{2\text{-}2}$ is
- (A) —H,
- (B) $C_1$-$C_8$ alkyl optionally substituted with 1 thru 4
  - (1) —F,
  - (2) —Cl,
  - (3) —$OR_{2\text{-}10}$ where $R_{2\text{-}10}$ is as defined above,
  - (4) —N $(R_{2\text{-}14})_2$ where $R_{2\text{-}14}$ may be the same or different and is as defined above, or $R_{2\text{-}1}$ and $R_{2\text{-}2}$ are taken together with the attached nitrogen atom to form a heterocyclic ring selected from the group consisting of
  - (A) 1-pyrrolidinyl optionally substituted on carbon with 1 thru 3 $R_{2\text{-}3}$ where $R_{2\text{-}3}$ is selected from the group of
    - (1) $C_1$-$C_6$ alkyl optionally substituted with 1 thru 3 —OH or —$OCH_3$,
    - (2) $C_1$-$C_6$ alkenyl optionally substituted with 1 thru 3 —OH or —$OCH_3$,
    - (3) $C_1$-$C_6$ alkylcarbonyl,
    - (4) $C_1$-$C_6$ alkoxycarbonyl,
    - (5) $C_6$-$C_{12}$arylalkyl,
    - (6)=O,
    - (7) —OH,
    - (8) —C≡N,
    - (9) —$CO_2R_{2\text{-}4}$ where $R_{24}$ is
      - (a) —H,
      - (b) $C_1$-$C_4$ alkyl,
      - (c) $C_6$-$C_{12}$aryl,
      - (d) $C_6$-$C_{12}$aralkyl,
    - (10) —$NH_2$,
    - (11) —Cl,
    - (12) —F,
    - (13) —Br,
    - (14) —φ optionally substituted with 1 thru 3 —F, —Cl, —Br, —OH, —$OCH_3$, —$OCH_2$—φ, —$NO_2$, $C_1$-$C_3$ alkyl, —$NH_2$, —$NHCH_3$, $N(CH_3)_2$, —$CO_2R_{2\text{-}4}$ where $R_{2\text{-}4}$ is as defined above,
    - (15) —$(CH_2)_{n4}NR_{2\text{-}6}R_{2\text{-}7}$ where $R_{2\text{-}6}$ and $R_{2\text{-}7}$ are the same or different and are $C_1$-$C_4$ alkyl or may taken together with the attached nitrogen atom to form the heterocyclic ring —N —$(CH_2)_{n5}$—$R_{2\text{-}8}$—$(CH2)_{n6}$* where the atoms marked with an asterisk (*) are bonded together resulting in the formation of a ring, where $n_4$ is 0 thru 3, $n_5$ is 1 thru 5, $n_6$ is 0 thru 3 and $R_{2\text{-}8}$ is
      - (a) —$CH_2$—,
      - (b) —O—,
      - (c) —S—,
      - (d) —N $R_{24}$ where $R_{2\text{-}4}$ is as defined above,
- (B) 1-piperdinyl optionally substituted on carbon with 1 thru 3 $R_{2\text{-}3}$ where $R_{2\text{-}3}$ is as defined above,
- (C) 1-morpholinyl optionally substituted on carbon with 1 thru 3 $R_{2\text{-}3}$ where $R_{2\text{-}3}$ is as defined above,
- (D) 1-piperazinyl optionally substituted on carbon with 1 thru 3 $R_{2\text{-}3}$ where $R_{2\text{-}3}$ is as defined above and optionally substituted in the 4-position with $R_{2\text{-}5}$ where $R_{2\text{-}5}$ is
  - (1) $C_1$-$C_6$ alkyl optionally substituted with 1 thru 3 —OH or —$OCH_3$,
  - (2) $C_1$-$C_6$ alkylcarbonyl,
  - (3) $C_1$-$C_6$ alkoxycarbonyl,
  - (4) $C_6$-$C_{12}$arylalkyl,
  - (5) —φ,
  - 20 (6) —$SO_2$-$C_1$-$C_8$ alkyl,
  - (7) 2— where the carbon atoms marked by an asterisk (*) are attached by a double bond to form a five member ring,
- (E) 1-aziridinyl optionally substituted on carbon with 1 thru 2$R_{2\text{-}3}$ where $R_{2\text{-}3}$ is as defined above,
- (F) 1-azetidinyl optionally substituted on carbon with 1 thru 3 $R_{2\text{-}3}$ where $R_{2\text{-}3}$ is as defined above,
- (G) 1-hexamethyleneimino optionally substituted on carbon with 1 thru 3 $R_{2\text{-}3}$ where $R_{2\text{-}3}$ is as defined above,
- (H) 1-pyrrolyl optionally substituted on carbon with 1 thru 3 $R_{2\text{-}3}$ where $R_{2\text{-}3}$ 30 is as defined above,
- (I) 1-imidazolyl optionally substituted on carbon with 1 thru 3 $R_{2\text{-}3}$ where $R_{2\text{-}3}$ is as defined above,
- (J) 1-pyrazoyl optionally substituted on carbon with 1 thru 3 $R_{2\text{-}3}$ where $R_{2\text{-}3}$ is as defined above,
- (K) 1-pyrazolidinyl optionally substituted on carbon with 1 thru 3 $R_{2\text{-}3}$ where $R_{2\text{-}3}$ is as defined above,
- (L) 1, 2, 3-triazolyl optionally substituted on carbon with 1 thru 3 $R_{2\text{-}3}$ where $R_{2\text{-}3}$ is as defined above,
- (M) 1, 2, 4-triazolyl optionally substituted on carbon with 1 thru 3 $R_{2\text{-}3}$ where $R_{2\text{-}8}$ is as defined above,
- (N) 1-tetrazolyl optionally substituted on carbon with 1 thru 3 $R_{2\text{-}3}$ where $R_{2\text{-}3}$ is as defined above,
- (O) 1-thiomorpholinyl optionally substituted on carbon with 1 thru 3 $R_{2\text{-}3}$ where $R_{2\text{-}3}$ is as defined above,
- (P) 1-thiazolidinyl, optionally substituted on carbon with 1 thru 3 $R_{2\text{-}3}$ where $R_{2\text{-}3}$ is as defined above.

(Q) ($R_{2\text{-}1}/R_{2\text{—}2}$-1)

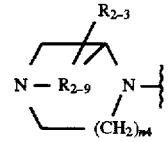

(R) ($R_{2\text{-}1}/R_{2\text{—}2}$-2)

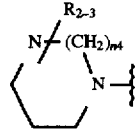

(S) ($R_{2\text{-}1}/R_{2\text{—}2}$-3)

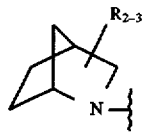

(T) ($R_{2\text{-}1}/R_{2\text{—}2}$-4)

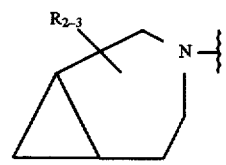

(U) ($R_{2\text{-}1}/R_{2\text{—}2}$-5)

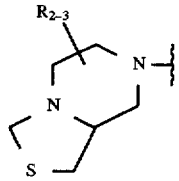

-continued (V) ($R_{2-1}/R_{2-2}$-6)
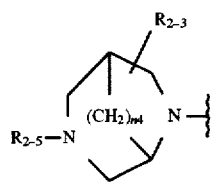

(W) ($R_{2-1}/R_{2-2}$-7)
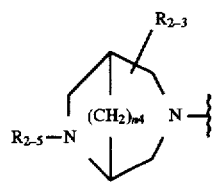

(X) ($R_{2-1}/R_{2-2}$-8)
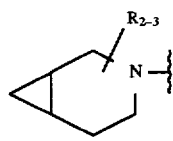

(Y) ($R_{2-1}/R_{2-2}$-9)
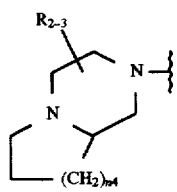

(Z) ($R_{2-1}/R_{2-2}$-10)
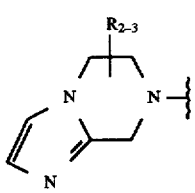

(AA) ($R_{2-1}/R_{2-2}$-11)
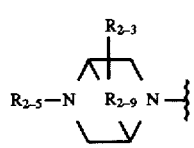

(BB) ($R_{2-1}/R_{2-2}$-12)
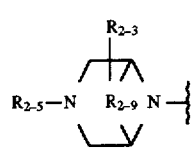

-continued (CC) ($R_{2-1}/R_{2-2}$-13)
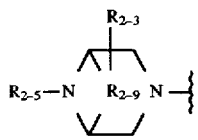

where $R_{2-8}$ and $R_{2-5}$ are as defined above,
where R is
(A)—$(CH_2)_{n4}$ where $n_4$ is 1 thru 3.
(B)—$CH_2OCH_2$,
(C)—$CH_2SCH_2$,
(D)—$CH_2So_2CH_2$,
(E)—$CH_2S$,
(F)—$CH_2SO_2$,
(G)—$CH_2N(R_{2-5})CH_2$ where $R_{2-5}$ is as defined above,
where $R_{4-1}$ is defined the same as $R_{2-1}$, but may be the same or different than $R_{2-1}$.
where $R_{4-2}$ is defined the same as $R_{2-2}$, but may be the same or different than $R_{2-2}$; and pharmaceutically acceptable salts thereof

DETAILED DESCRIPTION OF THE INVENTION

International Publication No. WO93/20078 discloses compounds which are bicyclic heterocyclic amines (XXX). The compounds of the present invention are a selection invention of International Publication No. WO93/20078 when $W_1$ and $W_3$ are both —N═and where $R_5$ and $R_6$ are taken together with the attached carbon atom to form a ring which is —C*—$CR_{56-1}$═$CR_{56-2}$—$CR_{56-3}$═$CR_{56-4}$—C*— where the carbon atoms marked by an asterisk (*) are bonded together by a double bond (C═C), where $R_{56-1}$, $R_{56-2}$, $R_{56-3}$ and $R_{56-4}$ are all —H.

The pyrimido[4, 5-b]indoles (I) of the present invention are made by the general processes set forth in International Publication No. WO93/20078 and by means well known to those skilled in the art.

The starting point in the synthesis of the pharmacologically active pyrimido[4, 5-b]indoles (I) is the halogenated ($X_1$ is —Cl or —Br) diaminopyrimidine (II). It is preferred that $X_1$ be —Cl. Before forming the 5-member ring, the final desired amino substituents (—N $R_{2-1}R_{2-2}$ and —N $R_{4-1}R_{4-2}$) on the pyrimidine ring are added or formed. The substituents —N $R_{2-1}R_{2-2}$ and —N $R_{4-1}R_{4-2}$ may be the same or different; it is preferred that they be the same for simplicity of chemical synthesis. The formation of the tertiary amines (—N R2-$_1R_{2-2}$, —N $R_{4-1}R_{4-2}$) from halogenated aromatic/ heteroaromatic compounds is known to those skilled in the art, see J. Med. Chem., 33, 1145 (1990). Generally, after the desired amino groups at the $C_2$ and $C_4$ positions are formed, and the $R_7$ substituent is introduced, the 5-membered ring is formed.

With the —N R2-1$NR_{2-2}$ and $NR_{4-1}R_{4-2}$ groups, it is preferred that the $R_{2-1}$ and $R_{2-2}$ are taken together with the attached nitrogen atom to form a heterocyclic ring. It is preferred that the heterocyclic ring be selected from the group consisting of 1-pyrrolidinyl, 1-piperidinyl, 4-morpholinyl, 4-methylpiperazinyl, 4-thiomorpholinyl, 1-piperazinyl. It is more preferred that $R_{2-1}$ and $R_{2-2}$ form 1-pyrrolidinyl or 1-piperazinyl, it is even more preferred that $R_{2-1}$ and $R_{2-2}$ form 1-pyrrolidinyl. Similarly, it is preferred that $R_{4-1}$ and $R_{4-2}$ be cyclized to form the same rings as for $R_{2-1}$ and $R_{2-2}$. The heterocyclic rings formed by $R_{2-1}/R_{2-2}$, and $R_{4-1}/R_{4-2}$ can be substituted with 1 thru 3 groups, $R_{2-3}$. When $R_{2-3}$ is a more than two such groups can be on any one carbon atom in the ring. When $R_{2-3}$ is other than alkyl, only one such group can be on any one carbon atom. It is well known how to prepare these groups, see for example U.S. Pat. No. 5,175,281 which discloses how to prepare numerous diaminosubstituted pyrimidines such as bis(1-pyrrolidinyl)pyrimidine.

CHART A discloses a general process for transformation of the appropriate diaminopyrimidine (II) to the corresponding pyrimido[4,5-b]indoles (I), for all $R_7$ except where $R_7$ is —H. CHART B discloses a more specific process for transformation of the appropriate diaminopyrimidine (II) to the corresponding pyrimido[4,5-b]indoles (I), where $R_7$ is —CH$_2$—CH$_2$—[substituent]. CHART C discloses a specific process for transformation of the appropriate diaminopyrimidine (II) to the corresponding pyrimido[4,5-b]indoles (I), where $R_7$ is —H. It is preferred that $R_7$ is 2-(4-morpholinyl) ethyl, 2-(1-imidazolyl)ethyl and 2-(1-piperidinyl)ethyl; it is more preferred that $R_7$ is 2-(4-morpholinyl)ethyl.

In CHART A the general process starts with the appropriate diaminopyrimidine (II) where $X_1$ is a leaving groups such as —Br or —Cl or the equivalent thereof. It is preferred that $X_1$ is —Cl. The diaminopyrimidine (II) is then converted to the corresponding triaminopyrimidine (III) by reaction with the appropriate $R_7$—NH amine by means known to those skilled in the art. With inexpensive, readily available amines, this can be accomplished by simply dissolving the diaminopyrimidine (II) in an excess of the $R_7$—NH$_2$ amine and heating. For hindered amines, the preformation of the anion $R_7$—NH— with a strong base such as butyl lithium enhances the nucleophilicity of the amine sufficiently. If it is desired to use less of the $R_7$—NH$_2$ amine, for whatever reason, a slight excess of the amine or its anion is all that is required and this can be heated in a solvent such as DMF, THF, xylene or the equivalent thereof. The addition of excess of a low molecular weight tertiary amine neutralizes the acid (hydrochloric) formed in the reaction. A suitable amine is triethylamine. The triaminopyrimidine (III) is then cyclized to form the corresponding saturated tricyclic compound (IV) by means known to those skilled in the art. This is accomplished by treatment of the triaminopyrimidine (III) with a-bromocyclohexanone (α-Chlorocyclohexanone is also operable) in the presence of an organic base such as triethylamine, diisopropylethylamine and the like in solvents such as THF, DMF, DMSO or acetonitrile. Acetonitrile is the preferred solvent. The necessary alkylation/cyclization/dehydration occurs by heating this mixture at reflux for 6–72hr. Slightly higher yields are obtained with the longer reaction times. The saturated tricyclic compound (IV) is isolated by crystallization or chromatography or may be carried on without isolation. Last the saturated tricyclic compound (IV) is dehydrogenated by known means such as DDQ, chloranil, or heating with palladium-on-Carbon catalysts in high boiling solvents such as decalin or diphenylether to produce the desired pyrimido[4,5-b]indoles (I).

With regard to the $R_7$ group, the preferred compounds of the invention are those where $R_7$ is $C_2$ alkyl substituted with a cyclized amino group. These compounds are best prepared by the process of CHART B. The process is much the same as with CHART A except the amino group reacted with the diaminopyrimidine (II) starting material is hydroxyethylamine (NH$_2$—CH$_2$—CH$_2$—OH) to form the hydroxyethyl diaminopyrimidine (VI). This material is cyclized to the corresponding hydroxyethyl saturated tricyclic compound (VII) and dehydrogenated to the corresponding hydroxyethyl unsaturated tricyclic compound (VIII) in the same way as previously described for CHART A. Following the formation of the unsaturated tricyclic ring system (VIII), the hydroxyl group is transformed to a good leaving group —X$_2$. This leaving group includes such items as halogen, sulfonate esters like methanesulfonate, and equivalent groups. The leaving group X$_2$ is replaced by "R" where $R_7$ is —CH$_2$—CH$_2$—R to form a preferred pyrimido[4,5-b] indoles (Ia).

The above described process incorporates the two double bonds in the last added ring prior to addition of the $R_7$ group. An alternate way to prepare the pyrimido[4,5-b]indoles (I) is to add the desired $R_7$ group prior to transforming the saturated six member ring to an unsaturated ring.

CHART C discloses how to make pyrimido[4,5-b]indoles (I), where $R_7$ is —H. To produce pyrimido[4,5-b]indoles (I) where $R_7$ is —H, the amine which is reacted with the diaminopyrimidine (II) starting material is t-butylamine forming the triaminopyrimidine (III) where the new substituent is —NH—(t-butyl). This t-butyl substituted triaminopyrimidine (III) is then cyclized and unsaturated as for the general process of CHART A to produce the t-butylsaturated tricyclic compound (XI) and the t-butylunsaturated tricyclic compound (XII). Lastly, the t-butyl group is replaced by —H to produce the pyrimido[4,5-b]indoles (Ib) by means known to those skilled in the art. Typical conditions involve heating the t-butylunsaturated tricyclic compound (XII) in a acidic medium, preferably trifluoroacetic acid, or concentrated aqueous hydrogen bromide or concentrated aqueous hydrogen chloride, and the like.

An alternative process for preparing the pyrimido[4,5-b] indoles (I) is by starting with trihalopyrimidines which are well known to those skilled in the art or are commercially available. The preferred 2,4,6-trihalopyrimidine is trichloropyrimidine. A mixture of the trihalopyrimidine in an inert solvent such as THF is allowed to react with 1 equivalent of a primary amine, $R_7$—NH$_2$ in the presence of an acid scavenger. Organic amines such as pyridine, triethylamine, diisopropylethylamine and inorganic bases such as potassium carbonate are useful acid scavengers. The reactants are mixed at a reduced temperature (—80° to 0°) and the reaction mixture is allowed to warm to room temperature (20–25°) and then is often concentrated at reduced pressure. The residue is partitioned between an organic solvent such as ethyl acetate or methylene chloride and an aqueous inorganic base such as potassium bicarbonate. The extract is dried, concentrated, and the residue chromatographed on silica gel to separate the desired 4-amino-pyrimidine. The 4-aminopyrimidine is mixed with an excess of a secondary amine, NHR$_{2-1}$R$_{2-2}$ and the mixture is heated under reflux for 2 to 24 hours. The mixture is allowed to cool and then is concentrated. The residue is partitioned as described above to remove the inorganic salts. The crude product is purified by conventional means (e.g. crystallization and/or chromatography) to give the desired trisubstituted pyrimidine. If a relatively nonvolatile secondary amine is used, the reaction mixture is diluted with an organic solvent such as ethyl acetate and the mixture is washed with an aqueous inorganic base. This provides a triaminopyrimidine (III) or (VI) in CHARTS A or B.

In some instances it may be desirable to modify the $R_7$ substituent after it is added to the tricyclic ring system rather than add the $R_7$ group in final form. For example, at the $R_7$ position the group may be a removable group such as tert-butyl or N-benzyl. Deprotection of such a compound by methods known to those skilled in the art will provide the —N—H analog. Alkylation, acylation, or other routine operations will provide compounds of formula (I) with a new $R_7$. Alternatively, the substituents at $R_7$ may contain a modifiable functional group that can produce new compounds containing altered $R_7$ substituents. The amine groups (—N $R_{2-1}R_{2-2}$, —N $R_{4-1}R_{4-2}$) may contain modifiable functional groups (possibly in a protected form) which can be modified as described above to form compounds containing new —N $R_{2-1}R_{2-2}$ and/or —N $R_{4-1}R4$–2 CHART D discloses the production of the lactam (XIII) from the corresponding hydroxyethyl unsaturated tricyclic compound (VIII) all by chemistry which is known to those skilled in the art, see *J. Heterocyclic Chem.* 10, 249 (1973). The free hydroxyl group of the hydroxyethyl unsaturated tricyclic compound (VIII) is converted to a good leaving group to form the hydroxyethyl unsaturated tricyclic compound with leaving group (IX) as is known to those skilled in the art. The hydroxyethyl unsaturated tricyclic compound with leaving group (IX) is reacted with ethanolamine to form the alcohol (XIV). The alcohol (XIV) is reacted with the dichloro compound, Cl—$CH_2$—CO—Cl (XV) to form the chloroalcohol (XVI) as is known to those skilled in the art. Finally the chloroalcohol (XVI) is cyclized by known means to form the lactam (XIII).

The pyrimido[4, 5-b]indoles (I) and the lactams (XIII) are amines, and as such form acid addition salts when reacted with acids of sufficient strength. Pharmaceutically acceptable salts include salts of both inorganic and organic acids. The pharmaceutically acceptable salts are preferred over the corresponding free amines since they produce compounds which are more water soluble and more crystalline. The preferred pharmaceutically acceptable salts include salts of the following acids hydrochloric, hydrobromic, sulfuric, phosphoric, nitric, citric, methanesulfonic, $CH3-(CH_2)_{n1}$—COOH where $n_1$ is 0 thru 4, HOOC—$(CH_2)n_1$—COOH where n is as defined above, HOOC—CH =CH—COOH, φ—COOH. For other acceptable salts, see *Int. J. Pharm.*, 33, 201–217 (1986).

Many of the pyrimido[4, 5-b]indoles (I) and the lactams (XIII) and pyrimido[4, 5-b]indoles (I) and the lactams (XIII) salts form hydrates and solvates either with one molecule of water or solvent or partial or multiples thereof. When the term pyrimido[4, 5-b]indoles (I) is used it means and includes the pharmaceutically acceptable salts thereof and the hydrated/solvated forms thereof where such exist.

It is preferred that the pyrimido[4, 5-b]indole (I) and the lactams (XIII) be selected from the compounds of EXAMPLEs 3, 5, 8, 10 and 30. It is more preferred that the pyrimido[4, 5-b]indole (I) be the compound of EXAMPLE 10, more preferably the salt of EXAMPLES 12 and 14, still more preferably the salt of EXAMPLE 12.

The pyrimido[4, 5-b]indoles (I) and the lactams (XIII) are useful in treating and/or preventing spinal injury mild and/or moderate to severe head injury, sub-arachnoid hemorrhage (SAH) and subsequent ischemic stroke, asthma and reduction of mucous formation/secretion in the lung, muscular dystrophy, adriamycin cardiac toxicity, Parkinsonism, other degenerative neurological disorders, multiple sclerosis, organ damage during reperfusion after transplant, preservation of transplant organs by treatment of the donor, skin graft rejection, hemorrhagic, traumatic and septic shock, and conditions such as severe burns, ARDS, chemical oxidant-induced injury to the kidney (for example, inhibition of contrast dye nephropathy and inhibition of cyclosporine toxicity) nephrotic syndrome (immunological), systemic lupus erythematosus, allergic reactions, atherosclerosis, inflammation (dermatological antiinflammatory and antipsoriasis agents), emphysema, cancer (limit metastasis, limit tumor growth), (stress induced) ulcers, ulcerative colitis and Crohn's disease. The compounds are also useful for prophylactic treatment before surgical procedures such as hip and jaw surgery where the pyrimido[4, 5-b]indoles (I) reduces edema. They are useful for preventing neurologic injury during surgical procedures and neurological procedures, for treatment of myocardial infarctions, for treatment after resuscitation to improve outcome, particularly neurological outcome post resuscitation, drug allergic reactions and migraine headaches. The compounds have use in ophthalmology, e.g., in treatment of diabetic retinopathy, age-related macular degeneration, cataracts and glaucoma, light-induced retinal damage and in irrigation mixtures used in eye surgery, prevention of hyperoxic injury in adults and infants, reduction of facial edema after surgical procedures such as oral/facial surgery or trauma from accidents. The pyrimido[4, 5-b]indoles (I) and the lactams (XIII) also can be co-administered with anti–Cancer drugs such as adriamycin, taxol or vinblastine when the tumor or cell strain becomes resistant as the pyrimido[4, 5-b]indoles (I) and the lactams (XIII) are an effective inhibitor of multiple drug resistance. The pyrimido[4, 5-b]indoles (I) and the lactams (XIII) are also useful in protection from radiation injury, particularly in brain and gut. In case of the gut, the pyrimido[4, 5-b]indoles (I) and the lactams (XIII) can be administered topically (e.g. by suppository) or by other more common routes. This is particularly helpful in preventing gut injury during prostate irradiation.

In humans, the pyrimido[4, 5-b]indoles (I) and the lactams (XIII) are useful in treating subarachnoid hemorrhage and subsequent cerebral vasospasm, global cerebral ischemia post resuscitation (CPR) to prevent post-ischemic brain damage, brain tumor (neuroprotective), Bells Palsy, other degenerative neurological disorders, hepatic necrosis (e.g. from viral hepatitis), some forms of radiation damage (for example during radiation treatment or from accidental exposure to radiation), myocardial damage after myocardial ischemia, pre-birth infant strangulation and infant hypoxia syndrome, such ophthalmic disorders as uveitis and optic neuritis and ischemic bowel syndrome.

In humans, the pyrimido[4, 5-b]indoles (I) and the lactams (XIII) are useful in preventing damage following cardiopulmonary resuscitation, neurological or cardiovascular surgery and from cardiac infarction, ocular damage after ophthalmic surgery (e.g. cataritic surgery).

The pyrimido[4, 5-b]indoles (I) and the lactams (XIII) are useful in treating complications of surgery or trauma such as edema and neurologic injury and renal injury.

Generally, the pyrimido[4, 5-b]indoles (I) and the lactams (XIII) are used like the glucocorticoid pharmaceuticals for the treatment of the above human conditions as well as the animal conditions listed below. While the pyrimido[4, 5-b]indoles (I) and the lactams (XIII) are useful in both humans and animals in treating many of the same conditions and preventing complications and damage from the same problems as the glucocorticoids, the pyrimido[4, 5-b]indoles (I) and the lactams (XIII) are useful in treating a number of conditions and preventing damage from conditions where the glucocorticoids are not useful. The pyrimido[4, 5-b]indoles (I) and the lactams (XIII) have no glucocorticoid activity and therefore, unlike the glucocorticoids, they can be given daily for longer periods of time without the side effects associated with the glucocorticoids. This is a distinct advantage. They have no effect on blood glucose and this is also an advantage.

It is to be understood that some of the pyrimido[4, 5-b]indoles (I) and the lactams (XIII) will be useful to a different degree to treat some of these conditions than others.

The standard conditions for treatment are to give the pyrimido|4, 5-b|indoles (I) and the lactams (XIII) orally or parenterally, e.g. IV (that is by injection, infusion or continuous drip) or IM, with a standard dose of about 5 to about 20 mg/kg/day IV for up to 20 days (with 10 days being sufficient for some conditions) or about 5 to about 30 mg/kg/day; one to four times daily by mouth. Females may be given higher doses than males since, on the average, they metabolize the pyrimido|4, 5-b|indoles (I) and the lactams (XIII) more rapidly than males. For females the standard dose is from about 7 to about 30 mg/kg/day IV or about 7 to about 50 mg/kg/day one to four times daily by mouth. For example, in treatment of SAH males may be give 10 mg/kg/day and women given 15 mg/kg/day. The dose can be administered as a single injection or, more typically, by divided doses (usually three or four times daily).

In treating SAH the patient should be treated with from about 6 mg/kg/day to about 20 mg/kg/day, preferably from about 10 to about 15 mg/kg/day.

In treating mild and moderate to severe head injury the patient should be treated with from about 5 mg/kg/day to about 50 mg/kg/day, preferably from about 10 to about 25 mg/kg/day.

In treating ischemic (thromboembolic) stroke the patient should be treated with an initial dose of from about 10 to about 25 mg/kg on day one, preferably from about 12.5 mg (males) and 15 mg (females) to about 20 mg/kg, to be followed by about 10 mg (males) and about 12.5 mg/kg (females) to about 20 mg/kg for about 3 days.

In treating spinal cord injury the patient is treated with about 5 to about 20 mg/kg/day for one to a few days. It is preferable to treat those with spinal cord injury with about 10 to about 20 mg/kg/day for one day. When treating patients with spinal cord injury it is also preferable to give them a one time large dose of a steroid such as methylprednisolone sodium succinate prior to the administration of the pyrimido[4,5-b]indoles (I) and the lactams (XIII).

For treating damage following cardiopulmonary resuscitation, cardiac infarction, organ damage during reperfusion after transplant, hemorrhagic, traumatic and septic shock, severe burns, ARDS, and nephrotic syndrome and preventing skin graft rejection, the standard conditions are used. Typical treatment may involve an initial loading dose, e.g. an IV dose of 0.05 mg to 4 mg/kg followed by maintenance dosing usually given four times a day by IV bolus infusion for one to 10 days depending on the particular condition of the patient and the particular compound used. This may be supplemented with IM or oral dosing for days, weeks or months.

The preferred use of the pyrimido[4,5-b]indoles (I) and the lactams (XIII) is to treat inflammatory lung maladies such as asthma. In treating asthma, the pyrimido[4,5-b] indoles (I) and the lactams (XIII) are administered orally, IV and by inhalation in the standard dose. It is preferred that the pyrimido|4,5-b|indoles (I) and the lactams (XIII) be administered either orally or by aerosol. For treating asthma, oral doses are about 5 to about 40 mg/kg/day given one to four times daily. In treating excess mucous secretions, the oral dose of the pyrimido|4,5-b|indoles (I) and the lactams (XIII) are from about 5 to about 30 mg/kg/day. The frequency of administration is one thru 4 times daily. The oral administration of the pyrimido|4,5-b |indoles (I) and the lactams (XIII) to treat excess mucous secretions may go on for months or even years. The susceptible individuals can be pre-treated a few hours before an expected problem. The IV dose is about 5 to about 20 mg/kg/day. The aerosol formulation contains about 0.01 to about 1.0% of the pyrimido|4, 5-b|indoles (I) and the lactams (XIII) are administered or used about four times daily as needed. In treating muscular dystrophy, Parkinsonism, and other degenerative neurological disorders (amyotrophic lateral sclerosis; multiple sclerosis) the pyrimido[4,5-b]indoles (I) and the lactams (XIII) are administered orally using a dose of about 5 to about 30 mg/kg/day, administered or used one to four times a day. The treatment may go on for years.

In treating adriamycin-induced cardiac toxicity, the pyrimido[4,5-b|indoles (I) and the lactams (XIII) are administered orally or IV using a dose of about 1.0 to about 50 mg/kg/day, preferably about 5 to about 20 mg/kg/day. The pyrimido[4,5-b]indoles (I) and the lactams (XIII) are preferably given concomitantly with IV adriamycin or the individual is pre-treated with the pyrimido|4,5-b|indoles (I) and the lactams (XIII).

For prophylaxis prior to and preventing damage after neurological or cardiovascular surgery, the pyrimido[4,5-b] indoles (I) and the lactams (XIII) are used according to the standard conditions. The patient can be pretreated with a single IV or IM dose just prior to and after surgery or orally before and after surgery.

In treating drug allergic reactions, the pyrimido[4,5-b| indoles (I) and the lactams (XIII) are given in a dose of about 5 to 20 mg/kg/day, administered one to four times daily IV and about 5 to about 30 mg/kg/day orally. Typical treatment would be an initial IV loading dose followed by oral dosing for a few days or more.

In treating atherosclerosis and emphysema, the pyrimido [4,5-b]indoles (I) and the lactams (XIII) are given orally in a dose of about 5 to about 30 mg/kg/day, one to four times daily for months or years. The pyrimido[4,5-b]indoles (I) and the lactams (XIII) are useful in treatment of premature infants who may be maintained in a high oxygen environment. The pyrimido[4,5-b]indoles (I) and the lactams ((XIII) improves morbidity and mortality in these cases which are paretically susceptible to intracranial bleeding and bronchopulmonary dysplasia. In this situation the standard treatment is given either IV or orally.

In treating dermatological inflammatory conditions including psoriasis, the pyrimido[4,5-b]indoles (I) and the lactams (XIII) are given orally in a dose of about 5 to about 30 mg/kg/day, once or the amount can be given two to four times daily in divided doses or applied topically as a cream, ointment or lotion or equivalent dosage form in a concentration of about 0.05 to about 5% as long as needed. In treating these conditions the pyrimido[4,5-b|indoles (I) and the lactams (XIII) can be used with steroidal agents.

The pyrimido[4,5-b]indoles (I) and the lactams (XIII) are useful in the prevention and treatment of stress ulcers and of gastric intolerance caused by drugs such as nonsteroidal anti-inflammatory compounds (NOSAC). Stress ulcers are ulcers that develop after exposure to severe conditions such as trauma, burns, sepsis, extensive surgery, acute illnesses, and the like. Patients in intensive care units are particularly prone to develop stress ulcers. Stress ulcers also include lesions that can lead to upper gastrointestinal bleeding; such bleeding is likely to be prevented by these compounds. NOSAC includes drugs such as ibuprofen, aspirin, indomethacin, naproxen, piroxicam and the like that are usually taken for analgesia, and that are often associated with gastrointestinal intolerance characterized by pain and lesions that may lead to bleeding. The pyrimido[4,5-b] indoles (I) and the lactams (XIII) will be administered preferentially by the oral route either as tablets, capsules or liquids, in doses ranging from about 25 to about 500 mg, two to four times a day. The treatment would be either preventive, i.e., starting before ulcers have formed in patients at risk of developing such lesions, or therapeutic, i.e., once the ulcers have formed. In patients whose clinical condition precludes swallowing the oral dosage forms, the pyrimido[4,5-b]indoles (I) and the lactams (XIII) are given either through a nasogastric tube, or parenterally, i.e., IV or IM. The parenteral doses would range from about 5 to about 100 mg and be administered one to four times a day or by IV.

In dogs, the pyrimido[4,5-b]indoles (I) and the lactams (XIII) are useful in treating trauma, intervertebral diseases (slipped disk), traumatic shock, flea bite and other allergies.

In horses, the pyrimido[4,5-b]indoles (I) and the lactams (XIII) are useful in treating endotoxic or septic shock which follows colic, pretreatment before surgery for colic and treatment of Founder (laminitis). The pyrimido[4,5-b]indoles (I) and the lactams (XIII) can reduce muscle damage that is a common occurrence during surgical procedures that require that the horse be prone for long periods during surgery.

In cattle, the pyrimido[4,5-b]indoles (I) and the lactams (XIII) are useful in treating acute coliform mastitis, bovine mastitis, acute allergic reaction to feed lot vaccination and shipping fever.

In pigs, the pyrimido[4,5-b]indoles (I) and the lactams (XIII) are useful in treating porcine stress syndrome and thermal stress syndrome.

The term treatment or treating as used in this patent is used broadly and includes both treatment of an existing condition as well as preventing the same condition from occurring where such is possible as is well known to those skilled in the art. For example, the pyrimido[4,5-b]indoles (I) and the lactams (XIII) can be used to treat existing asthma conditions and to prevent future ones from occurring. For example, the pyrimido[4,5-b]indoles (I) and the lactams (XIII) treats spinal trauma and prevent rejection of skin grafts.

The pyrimido[4,5-b]indoles (I) and the lactams (XIII) can be used with each other and/or can be used with other pharmaceutical agents in treatment of the conditions listed above as is known to those skilled in the art.

In many instances it may be preferable to administer an inhibitor of the pyrimido[4,5-b]indoles (I) and the lactams (XIII) metabolism, such as ketoconazole or TAO (triacetyloleandomycin) prior to or concurrently with the pyrimido[4,5-b]indoles (I) and the lactams (XIII) administration to raise the blood level of the pyrimido[4,5-b]indoles (I) and the lactams (XIII) and/or certain of its metabolites. Because females metabolize the pyrimido[4,5-b]indoles (I) and the lactams (XIII) more rapidly than males, administration of an inhibitor of the pyrimido[4,5-b]indoles (I) and the lactams (XIII) metabolism can raise blood levels in females to that of males. For example, ketoconazole should be administered in an amount of about 50 to about 300 mg/day, preferably about 200 mg/day about 1 to about 2 hr for acute uses and about 1 to about 3 hr for repeat dose situations.

The exact dosage and frequency of administration of the pyrimido[4,5-b]indoles (I) and the lactams (XIII) depends on the particular condition being treated, the severity of the condition being treated, the age, weight, general physical condition of the particular patient, other medication the individual may be taking as is well known to those skilled in the art and can be more accurately determined by measuring the blood level or concentration of the pyrimido[4,5-b]indoles (I) and the lactams (XIII) (or biologically active metabolite thereof) in the patient's blood and/or the patient's response to the particular condition being treated.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$," or "$R_i$," where "i" is an integer. These variable substituents are either monovalent or bivalent, that is, they represent a group attached to the formula by one or two chemical bonds. For example, a group Z, would represent a bivalent variable if attached to the formula $CH_3$—$C(=Z_1)$ H. Groups $R_i$ and $R_j$ would represent monovalent variable substituents if attached to the formula $CH_3$—$CH_2$—$C(R_i)$ ($R_j$) —H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$ —$CH_3$ represents a 2-substituted-i-methoxypropane compound. In a similar fashion, the symbol "=" represents a double bond, e.g., $CH_2$=$C(R_i)$ —O—$CH_3$, and the symbol "≡" represents a triple bond, e.g., HC≡C-$CH(R_i)$ —$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$) —CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)2—N($C_2H_5$) —$CH_2$—$C*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system. —C(X₁)(X₂)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents $\alpha$—$R_{i-j}$ and $\beta$—$R_{i-k}$. When a bivalent variable, $R_i$, is defined to consist of two monovalent variable substituents, the convention used to define the bivalent variable is of the form "$\alpha$—$R_{i-j}$:$\beta$—$R_{i-k}$" or some variant thereof. In such a case both $\alpha$—$R_{i-j}$ and $\beta$—$R_{i-k}$ are attached to the carbon atom to give —C($\alpha$—$R_{i-j}$)($\beta R_{i-k}$)—. For example, when the bivalent variable $R_6$, —C(=$R_6$)— is defined to consist of two monovalent variable substituents, the two monovalent variable substituents are $\alpha$—$R_{6-1}$:$\beta_{6-2}$, . . . $\alpha$—$R_{6-9}$: $\beta$—$R_{6-10}$, etc, giving —C($\alpha R_{6-1}$)($\beta$—$R_{6-2}$)—, . . . —C($\alpha$—$R_{6-9}$)($\beta$—$R_{6-10}$)—, etc. Likewise, for the bivalent variable $R_{11}$, —C(=$R_{11}$)—, two monovalent variable substituents are $\alpha$—$R_{11-1}$:$\beta$—$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H—($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —CH₂—CH₂—O—CO— . . ." means a lactone in which the carbonyl is bonded to $C_2$. However, when designated ". . . $R_j$ and $R_i$ are taken together to form —CO—O—CH₂—CH₂—the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$) alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

THF refers to tetrahydrofuran.

DMSO refers to dimethylsulfoxide.

DMF refers to dimethylformamide.

DDQ refers to 2,3-dichloro-5,6-dicyano-1,4-benzoquinone.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

NMR refers to nuclear (proton) magnetic resonance spectroscopy, chemical shifts are reported in ppm ($\delta$) downfield from tetramethylsilane.

TMS refers to trimethylsilyl.

$\phi$ refers to phenyl ($C_6H_5$).

MS refers to mass spectrometry expressed as m/e or mass/charge unit. [M+H]+ refers to the positive ion of a parent plus a hydrogen atom. E1 refers to electron impact. CI refers to chemical ionization. FAB refers to fast atom bombardment.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include mesylate, chloride, sulfate, phosphate, nitrate, citrate, $CH_3$—$(CH_2)$ $n_1$—COO—$^{-1}$ where $n_1$ is 0 thru 4, $^-$OOC— $(CH_2)n_1$—COO$^{-1}$ where n is as defined above, $^{-1}$OOC—CH=CH—COO$^{-1}$, $\phi$—COO$^{-1}$.

When solvent pairs are used, the ratios of solvents used are volume/volume (v/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

2-[(2,6-Di—(1-pyrrolidinyl)pyrimidin-4-yl)amino]ethanol (VI)

A mixture of 4-chloro-2,6-di-1-pyrrolidinyl-pyrimidine (II, *J. Med. Chem.*, 33, 1145 (1990), 300 g) in ethanolamine (1000 mL) is heated at 140° for 66 hr. The reaction mixture is cooled, diluted with water (1700 mL) and the product is isolated by filtration, to give the title compound, mp=150.5–151.50°; NMR (CDCl$_3$) 6.55, 4.83, 4.75, 3.75–3.72, 3.54–3.38 and 1.93–1.85 δ.

Example 2

9-(2-Hydroxyethyl)-2,4-di- 1-pyrrolidinyl-5,6,7,8-tetrahydro-9H-pyrimido[4,5-b]indole (VII)

A mixture of 2-[(2,6-di-(1-pyrrolidinyl)pyrimidin-4-yl)amino]ethanol (VI, Example 1, 5.55 g), 2-bromocyclohexanone (3.54 g), N,N-diisopropylethylamine (2.65 g) and acetonitrile (60 mL) is heated at reflux for 44 hr. The reaction mixture is cooled to 20°–25° and concentrated under reduced pressure. The residue is partitioned between methylene chloride and aqueous sodium bicarbonate solution. The organic phase is dried over sodium sulfate, filtered, and concentrated. Chromatography (silica gel, 2.5% acetone/chloroform) gives the title compound, NMR (CDCl$_3$) 7.64, 4.05, 3.91, 3.67, 3.55, 2.72, 2.56, 2.0–1.7 δ; MS (m/z) calc'd=355.2372, found=355.2368.

Example 3

9-(2-Hydroxyethyl)-2,4-di-1-pyrrolidinyl-9H-pyrimido[4,5-b]indole (VIII and I)

A mixture of 9-(2-hydroxyethyl)-2,4-di-1-pyrrolidinyl-5,6,7,8-tetrahydro-9H-pyrimido[4,5-b]indole (VII, EXAMPLE2, 5.14 g) and palladium on carbon (10%, 1.4 g) in decalin (250 mL) is heated at reflux for 3 hr. The mixture is cooled to 20°–25°, diluted with methylene chloride (250 mL) and filtered through diatomaceous earth. Removal of the solvent from the filtrate, followed by chromatography (silica gel, 1% methanol/chloroform) of the resulting residue gives the title compound, mp=110°–111; MS (m/z) 351, 323, 307, 296 and 279; NMR (CDCl$_3$) 7.89, 7.23, 7.13, 6.97, 4.38, 4.05, 3.92, 3.62 and 2.0–1.9 δ.

Example 4

9-(2-Methanesulfonyloxyethyl)-2,4-di-1-pyrrolidinyl-9H-pyrimido[4,5-b]indole (IX)

A mixture of methanesulfonyl chloride (0.38 mL) in methylene chloride (20 mL) is added dropwise to a mixture of 9-(2-hydroxyethyl)-2,4-di-1-pyrrolidinyl-9H-pyrimido[4,5-b]indole (VIII, EXAMPLE3, 1.05 g) and triethylamine (0.5 mL) in methylene chloride (25 mL). After a few minutes, the reaction mixture is diluted with water and extracted with methylene chloride. The organic layer is dried (sodium sulfate) and concentrated, to give the title compound.

Example 5

9-[2-(1-Piperidinyl)ethyl]-2,4-di-1-pyrrolidinyl-9H-pyrimido[4,5-b]indole (I)

A mixture of 9-(2-methanesulfonyloxyethyl)-2,4-di-1-pyrrolidinyl-9H-pyrimido[4,5-b]indole (IX, EXAMPLE4, 50 g) and piperidine (200 mL) is heated at reflux for 16 hr. Excess piperidine is removed under reduced pressure and the residue is partitioned between methylene chloride and aqueous sodium bicarbonate. The organic phase is washed with saline, dried over sodium sulfate and concentrated to give the title compound, NMR (CDCl$_3$) 7.88, 7.28, 7.20, 7.10, 4.46–4.40, 3.94–3.90, 3.66–3.62, 2.74–2.68, 2.57, 1.98–1.94, 1.64–1.58 and 1.45 δ.

Example 6

9-[2-(1-Piperidinyl)ethyl]-2,4-di-1-pyrrolidinyl-9H-pyrimido[4,5-b]indole monohydrochloride (I)

A mixture of 9-[2-(1-piperidinyl)ethyl]-2,4-di-1-pyrrolidinyl-9H-pyrimido[4,5-b]indole (I, EXAMPLE5, 44 g) and aqueous hydrochloric acid (1M, 107 mL) in ethanol (900 mL) is stirred at 60° until the mixture becomes homogeneous. The mixture is concentrated under reduced pressure in a stream of nitrogen. When the reaction volume reaches approximately half of the original volume, crystallization begins. The mixture is cooled to –10° for 3 hr and the title compound, is isolated by filtration, mp >260°; NMR (CDCl$_3$) 7.88, 7.52, 7.28, 7.13, 4.86, 3.94–3.89, 3.62, 3.45, 3.15 and 2.01–1.96 δ.

Example 7

9-(2-Hydroxyethyl)-2,4-di-1-pyrrolidinyl-9H-pyrimido[4,5-b]indole monohydrochloride (I)

Following the general procedure of EXAMPLE6, and making non-critical changes, but starting with 9-(2-hydroxyethyl)-2,4-di-1-pyrrolidinyl-9H-pyrimido[4,5-b]indole (VIII, EXAMPLE3), the title compound is obtained, mp=230°–232°.

Example 8

9-[2-(1-Imidazolyl)ethyl]-2,4-di-1-pyrrolidinyl-9H-pyrimido[4,5-b]indole (I)

A mixture of 9-(2-methanesulfonyloxyethyl)-2,4-di-1-pyrrolidinyl-9H-pyrimido[4,5-b]indole (IX, EXAMPLE4, 0.64 g), imidazole (1.02 g) and xylene (15 mL) is heated at reflux for 3 hr. The xylene is then removed under reduced pressure, and the residue is partitioned between methylene chloride and aqueous sodium bicarbonate. The organic phase is washed with saline, dried over sodium sulfate and concentrated. Chromatography (silica gel, 4% methanol/methylene chloride) gives the title compound, mp=181°–183°; NMR (CDCl$_3$) 7.88, 7.40, 7.14–7.09, 7.01–6.97, 6.82, 4.56–4.54, 4.44–4.42, 3.92, 3.63 and 1.99 δ.

Example 9

9-[2-(1-Imidazolyl)ethyl]-2,4-di-1-pyrrolidinyl-9H-pyrimido[4,5-b]indole sulfuric acid salt (I)

A mixture of 9-[2-(1-imidazolyl)ethyl]-2,4-di-1-pyrrolidinyl-9H-pyrimido[4,5-b]indole (I, EXAMPLE8, 0.334 g), sulfuric acid (0.5M, 1.73 mL), water (2 mL) and 2-propanol (20 mL) is warmed gently until the mixture becomes homogeneous. Following removal of the solvents at reduced pressure, the solid product is recrystallized from ethanol/acetone to give the title compound, mp=262°–263°.

Example 10

9-|2-(4-Morpholinyl)ethyl|-2,4-di-1-pyrrolidinyl-9H-pyrimido|4,5-b|indole (I)

Following the general procedure of EXAMPLE5 and making non-critical variations but utilizing morpholine instead of piperidine, the title compound is obtained, mp=138°–139°; MS (m/z) calc'd=420.2637, found=420.2640; NMR (CDCl$_3$) 7.90, 7.25, 7.19, 7.10, 4.45, 3.92, 3.70, 3.62, 2.75, 2.62 and 2.05–1.90 δ.

Example 11

9-|2-(4-Morpholinyl)ethyl|-2,4-di-1-pyrrolidinyl-9H-pyrimido|4,5-bindole, monohydrochloride anhydrous (I)

A mixture of 9-|2-(4-morpholinyl)ethyl]-2,4-di-1-pyrrolidinyl-9H-pyrimido|4,5-bindole (I, EXAMPLE10, 2.77 g), methanolic hydrogen chloride (0.65M, 10.15 mL) ethyl acetate (70 mL) is warmed gently until the solution is homogeneous. Shortly thereafter, the title salt precipitates and is isolated by filtration, mp=246°–247°.

Example 12

9-|2-(4-Morpholinyl)ethyl|-2,4-di-1-pyrrolidinyl-9H-pyrimido|4,5-bindole, monohydrochloride hemihydrate (I)

A mixture of 9-[2-(4-morpholinyl)ethyl]-2,4-di-1-pyrrolidinyl-9H-pyrimido|4,5-b]indole (I, EXAMPLE10, 64.1 g), ethanol (950 mL), water (50 mL) and aqueous hydrochloric acid (37%, 12.5 mL) is heated gently until the mixture becomes homogeneous. Upon cooling, the title compound crystallizes and is isolated by filtration, mp=230°.

Example 13

9-|2-(4-Morpholinyl)ethyl|-2,4-di-1-pyrrolidinyl-9H-pyrimido[4,5-b]indole, dihydrochloride (I)

A mixture of 9-[2-(4-morpholinyl)ethyl]-2,4-di-1-pyrrolidinyl-9H-pyrimido[4,5-bindole (I, EXAMPLE10, 420 mg), 2 mL of methanol and 5 mL of 0.43M methanolic hydrochloric acid is heated until it becomes homogeneous. The solvent is removed by careful distillation, replacing with ethyl acetate until crystallization begins. After cooling, the title compound is isolated by filtration, mp=255°–257°.

Example 14

9-[2-(4-Morpholinyl)ethyl]-2,4-di-1-pyrrolidinyl-9H-pyrimido|4,5-b]indole, sulfate (I)

Following the general procedure of EXAMPLE9 and making non-critical variations but starting with 9-[2-(4-morpholinyl)ethyl]-2,4-di-1-pyrrolidinyl-9H-pyrimido[4,5-b|indole (I, EXAMPLE10), the title compound is obtained, mp=218°–219°.

Example 15

9-|2-(4-Morpholinyl)ethyl|-2,4-di-1-pyrrolidinyl-9H-pyrimido|4,5-bindole, monocitrate (I)

A mixture of 9-|2-(4-morpholinyl)ethyl]-2,4-di-1-pyrrolidinyl-9H-pyrimido|4,5-b|indole (I, EXAMPLE10, 420 mg), 210 mg of citric acid monohydrate and 10 mL of methanol is heated until it becomes homogeneous. Following evaporation of the methanol under reduced pressure, the residue is triturated with ether, then filtered to give the title compound, mp=168°–170°.

Example 16

9-|2-(4-Morpholinyl)ethyl|-2,4-di-1-pyrrolidinyl-9H-pyrimido|4,5-b|indole, dicitrate (I)

Following the general procedure of EXAMPLE15 and making non-critical variations, but utilizing two equivalents of citric acid, the title compound is obtained, mp=161°–163°.

Example 17

9-|2-(4-Morpholinyl)ethyl|-2,4-di-1-pyrrolidinyl-9H-pyrimido|4,5-b|indole, monomethanesulfonate (I)

A mixture of 9-|2-(4-morpholinyl)ethyl]-2,4-di-1-pyrrolidinyl-9H-pyrimido|4,5-b|indole (I, EXAMPLE10, 1.0 g), 0.228 g of methanesulfonic acid, and isopropyl alcohol/water (95/5, 55 mL) is warmed until the mixture becomes homogeneous. Following removal of the solvents under reduced pressure, recrystallization from acetone gives the title compound, mp=223°–225°.

Example 18

9-[2-(4-Morpholinyl)ethyl]-2,4-di-1-pyrrolidinyl-9H-pyrimido[4,5-b]indole, dimethanesulfonate (I)

Following the general procedure of EXAMPLE17 and making non-critical variations but utilizing two equivalents of methanesulfonic acid, the title compound is obtained, mp=170°–172°.

Example 19

9-[2-(4-Morpholinyl)ethyl]-2,4-di-1-pyrrolidinyl-9H-pyrimido[4,5-b]indole, maleate (I)

Following the general procedure of EXAMPLE13 and making non-critical variations but utilizing one equivalent of maleic acid in place of methanolic hydrochloric acid, the title compound is obtained, mp=190°.

Example 20

9-[2-(4-Morpholinyl)ethyl]-2,4-di-1-pyrrolidinyl-9H-pyrimido[4,5-b]indole, hydrobromide (I)

Following the general procedure of EXAMPLE12 and making non-critical variations but utilizing one equivalent of aqueous hydrogen bromide instead of hydrogen chloride, the title compound is obtained, mp=267°.

Example 21

5,6,7,8-Tetrahydro-9-|2-(4-morpholinyl)ethyl]-2,4-di-1-pyrrolidinyl-9H-pyrimido|4,5-b|indole Following the general procedures of EXAMPLEs 4 and 10 and making non-critical variations, but starting with 9-(2-hydroxyethyl)-2,4-di-1-pyrrolidinyl-5,6,7,8-tetrahydro-9H-pyrimido|4,5-b|indole (VII, EXAMPLE 2), the title compound is obtained, mp=132°–133°; MS (m/z) 424, 312, 311, 283 and 100; NMR (CDCl$_3$) 4.10, 3.73–3.65, 3.56–3.54, 2.72–2.56 and 1.94–1.75 67 .

Example 22

9-[2-(4-Morpholinyl)ethyl]-2,4-di-1-pyrrolidinyl-9H-pyrimido[4,5-b]indole (I)

Following the general procedure of EXAMPLE 3 and making non-critical variations, but starting with 5,6,7,8-tetrahydro-9-[2-(4-morpholinyl)ethyl]-2,4-di-1-pyrrolidinyl-9H-pyrimido[4,5-b]indole (EXAMPLE 21), the title compound is obtained, mp=138–139°; NMR (CDCl₃) 7.90, 7.25, 7.19, 7.10, 4.45, 3.92, 3.70, 3.62, 2.75, 2.62 and 2.05–1.90 δ.

Example 23

4-(t-Butylamino)-2,6-di-1-pyrrolidinylpyrimidine (X)

A mixture of 21.7 g of t-butylamine in 100 mL of tetrahydrofuran is cooled to about –40° and treated over about 15 min with 170 mL of 1.6M n-butyllithium in hexane. The mixture is warmed to 0° for 2 hr, then recooled to –40° and treated over 30 min with a mixture of 25 g of 4-chloro-2, 6-di-1-pyrrolidinylpyrimidine and 50 mL of tetrahydrofuran. The mixture is allowed to warm to 20°–25° and is stirred for 16–18 hr. Water (50 mL) is then added and the mixture is concentrated under reduced pressure. The residue is partitioned between methylene chloride and aqueous 10% sodium bicarbonate. The organic phase is washed with saline, dried over anhydrous sodium sulfate and concentrated. Chromatography (silica gel, 5% ethyl acetate/hexane) gives the title compound, NMR (CDCl₃) 4.78, 4.25, 3.53–3.49, 3.40, 1.93–1.86 and 1.41 δ.

Example 24

5,6,7,8-Tetrahydro-9-t-butyl-2,4-di-1-pyrrolidinyl-9H-pyrimido[4,5-b]indole (XI)

Following the general procedure of EXAMPLE 2 and making non-critical variations, but starting with 4-(t-butylamino)-2,6-di-1-pyrrolidinylpyrimidine (X, EXAMPLE 23), the title compound is obtained, NMR (CDCl₃) 3.68–3.64, 3.59–3.55, 2.91–2.87, 2.76–2.72, 1.94–1.85, 1.82, 1.67–1.64 δ.

Example 25

9-t-Butyl-2,4-di-1-pyrrolidinyl-9H-pyrimido[4,5-b]indole (XII)

Following the general procedure of EXAMPLE 3 and making non-critical variations, but starting with 5,6,7,8-tetrahydro-9-t-butyl-2,4-di-1-pyrrolidinyl-9H-pyrimido[4,5-b]indole (XI, EXAMPLE 24), the title compound is obtained, NMR (CDCl₃) 7.79–7.74, 7.12–7.08, 3.82–3.77, 3.65–3.61, 2.00 and 2.07–1.89 δ.

Example 26

2,4-Di-1-pyrrolidinyl-9H-pyrimido[4,5-b]indole (Ib)

A mixture of 9-t-butyl-2,4-di-1-pyrrolidinyl-9H-pyrimido[4,5-b]indole (XII, EXAMPLE 25, 4.0 g) and 100 mL of trifluoroacetic acid is heated at reflux for 2 hr. Approximately one-half of the trifluoroacetic acid is removed by distillation. The reaction mixture is then cooled to 0°, made basic with 25% aqueous sodium hydroxide and extracted with methylene chloride. The combined organic phases are washed with saline, dried over anhydrous sodium sulfate and concentrated. Chromatography (silica gel, 5% ethyl acetate/methylene chloride) gives the title compound, NMR (CDCl₃) 7.89, 7.86, 7.26–7.09, 3.95, 3.67 and 2.01–1.95 δ.

Example 27

2,4-Di-1-pyrrolidinyl-9H-pyrimido[4,5-b]indole, monohydrochloride (Ib)

Following the general procedure of EXAMPLE 6 and making non-critical variations, but starting with 2,4-di-1-pyrrolidinyl-9H-pyrimido[4,5-b]indole (Ib, EXAMPLE 26), the title compound (salt) is obtained, mp=303°–306°; NMR (CDCl₁) 7.93, 7.90, 7.47, 7.44, 7.31–7.20, 4.60–3.60 and 2.20–1.90 δ.

Example 28

9-[2-(2-Hydroxyethylamino)ethyl]-2,4-di-1-pyrrolidinyl-9H-pyrimido[4,5-b]indole (XIV)

A mixture of 9-(2-methanesulfonyloxyethyl)-2,4-di-1-pyrrolidinyl-9H-pyrimido[4,5-b]indole (IX, EXAMPLE 4, 1.3 g) and 15 ml of ethanolamine is heated to reflux for 4 hr, then cooled, and diluted with methylene chloride (100 mL) and aqueous saturated sodium bicarbonate. The phases are separated, and the aqueous phase is extracted again with methylene chloride/chloroform (1/1). The combined extracts are dried over sodium sulfate and concentrate under reduced pressure at 50°–60° to give a solid. The solid is recrystallized from ethyl acetate/hexane at 20°–250 to give the title compound, NMR (CDCl₃) 1.5–1.7, 1.9–2.0, 2.84, 3.12, 3.56, 3.63, 3.92, 4.20, 7.10, 7.13–7.30 and 7.80 δ; MS (EI, m/z) 394 (M+), 363, 320 and 307.

Example 29

9-[2-(2-hydroxyethylamino)ethyl]-2,4-di-1-pyrroldinyl-9H-pyrimido[4,5-b]indole chloroacetylamide (XVI)

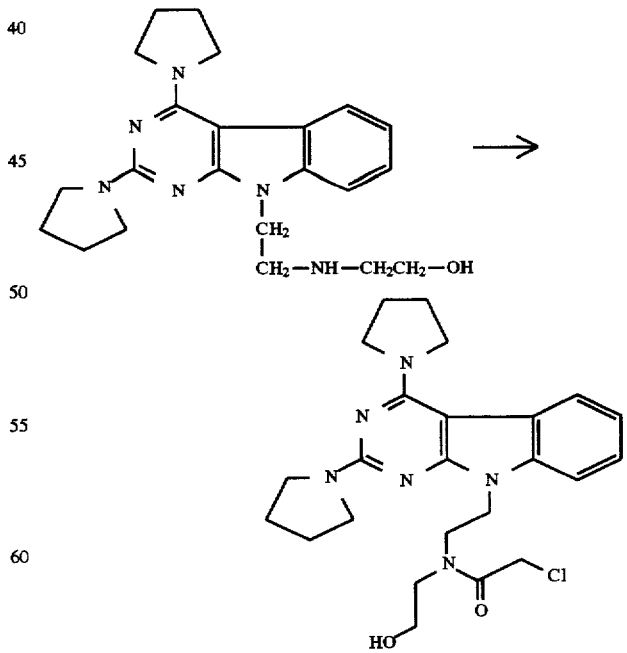

A solution of chloroacetyl chloride (0.68 g, 5.99 mmol) in methylene chloride (10 mL) is added dropwise to a solution of 9-[2-(2-hydroxyethylamino)ethyl]-2,4-di-1-pyrrolidinyl-9H-pyrimido[4,5-b]indole (XIV, EXAMPLE 28, 2.15 g, 5.45 mmol) and triethylamine (1.13 mL, 8 mmol) in methylene chloride (40 mL) at −780. The mixture is stirred at −78° for 1 hr and then allowed to warm to 0°. The mixture is diluted additional methylene chloride and aqueous saturated sodium bicarbonate. The phases are separated and the organic phase is dried over sodium sulfate, and concentrated under reduced pressure to give 2.6 g of crude product. TLC (silica gel GF; methanol/methylene chloride (10/90)): $R_f$=0.33 major spot and $R_f$=0.83 minor spot (UV & $I_2$); NMR (CDCl$_3$) 1.97, 3.35, 3.61, 3.78, 3.82, 3.90, 4.55, 7.11, 7.20–7.35 and 7.88 δ. No further purification of the product was performed and it is utilized in the subsequent cyclization reaction.

Example 30

9-[2-(3-Oxo-4-morpholinyl)ethyl]-2,4-di-1-pyrrolidinyl-9H-pyrimido[4,5-b]indole (XIII)

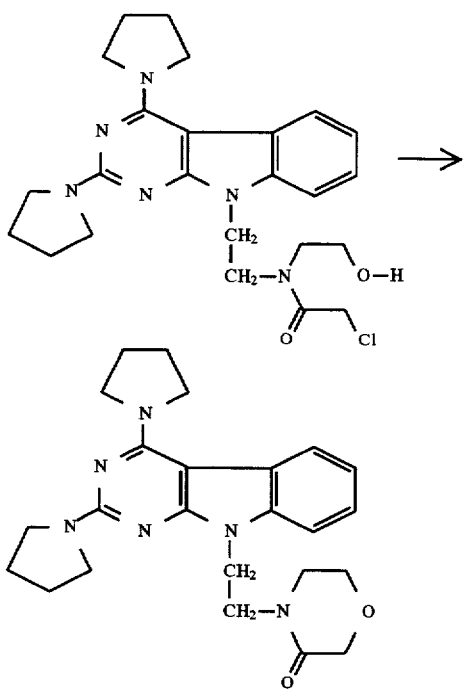

A solution of potassium tert-butoxide in THF (1M, 7 mL, 7 mmol) is added to a stirred solution of 9-[2-(2-hydroxyethylamino)ethyl]-2,4-di-1-pyrroldinyl-9H-pyrimido[4,5-b]indole chloroacetylamide (XVI, EXAMPLE 29, 5.4 mmol) in THF (25 mL) at 0 and then stirred at 20°–250 for 15 min. The reaction mixture is diluted with water and ethyl acetate (100 mL). The phases are separated and the organic phase is washed with aqueous potassium carbonate, water and aqueous saturated sodium chloride, dried over sodium sulfate and concentrated under reduced pressure. The concentrate is flash chromatographed (silica gel 60; methanol/methylene chloride, 2/98) to give a solid which is crystallized from acetone to give the title compound, mp=179–180°; NMR (CDCl$_3$) 1.98, 2.74, 3.20, 3.64, 3.79, 3.91, 4.04, 4.57, 7.10, 7.21, 7.33 and 7.88 δ; IR (mull) 1660, 1647, 1610, 1583, 1542, 1522, 1488, 1433, 1426, 1344, 1308, 1221, 1112, 789 and 741 cm$^{-1}$; MS (EI, m/z) 434 (M+), 435, 434, 379, 320, 308, 307, 279, 128, 70 and 56.

Example 31

9-[2—(3-Oxo-4-morpholinyl)ethyl]-2,4-di-1-pyrrolidinyl-9H-pyrimido[4,5-b]indole hydrochloride (XIII)

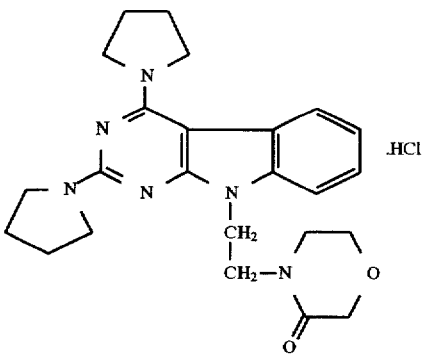

A hot solution of 9-[2—(3-Oxo-4-morpholinyl)ethyl]-2,4-di-1-pyrrolidinyl-9H-pyrimido[4,5-b]indole (XIII, EXAMPLE30, 0.91 g, 2.1 mmol) in ethanol (60 mL) is treated with aqueous hydrochloric acid (5M, 0.43 mL, 2.15 mmol). The mixture is cooled to 20°–250° and concentrated under reduced pressure to a solid. Recrystallization of the solid from acetone/methanol/ether gives the title compound, mp=210°–213°; IR (mull) 1651, 1631, 1573, 1554, 1527, 1499, 1486, 1436, 1415, 1353, 1339, 1312, 1241, 1110 and 772 cm$^{-1}$.

CHART A

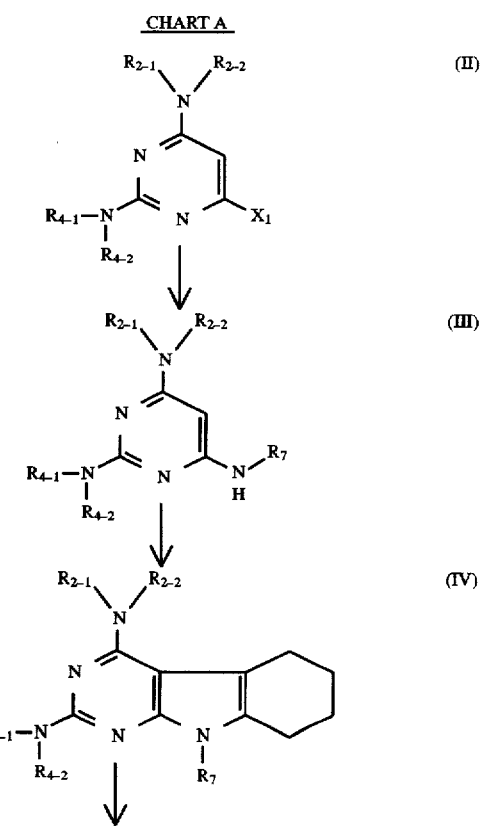

CHART A
-continued
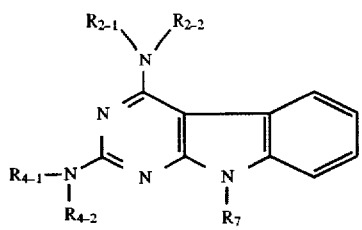
(I)
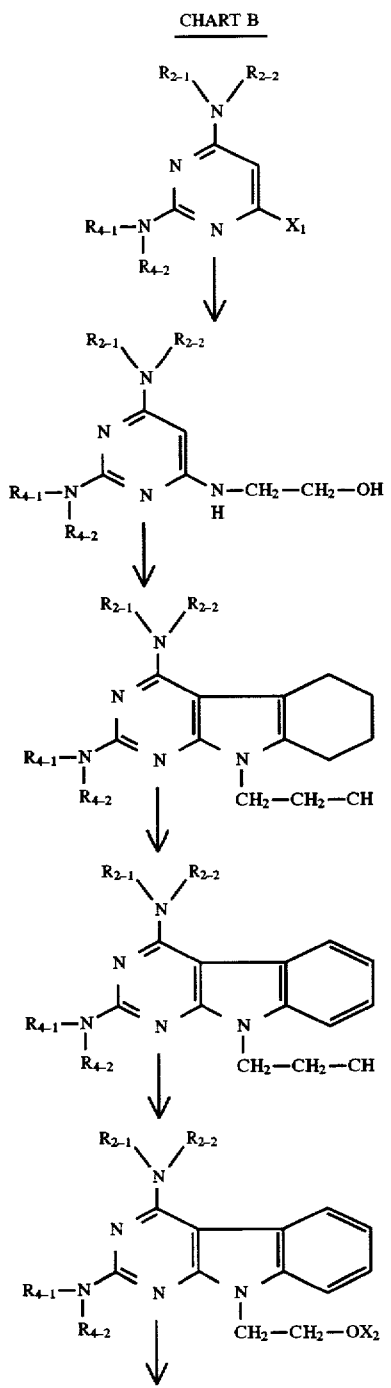
(II)
(VI)
(VII)
(VIII)
(IX)
CHART B
-continued
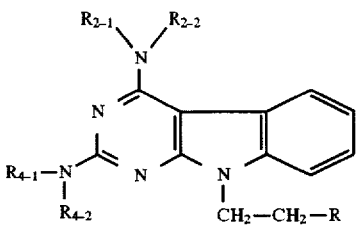
(Ia)
CHART C
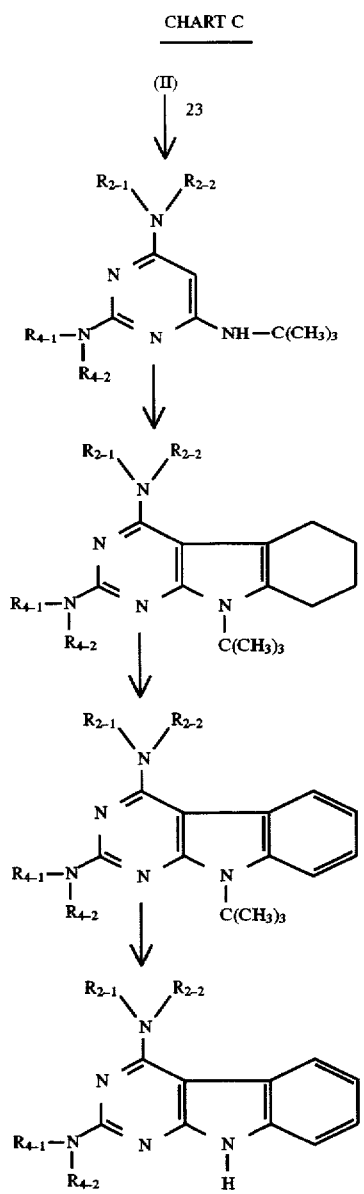
(II)
(X)
(XI)
(XII)
(Ib)

CHART D

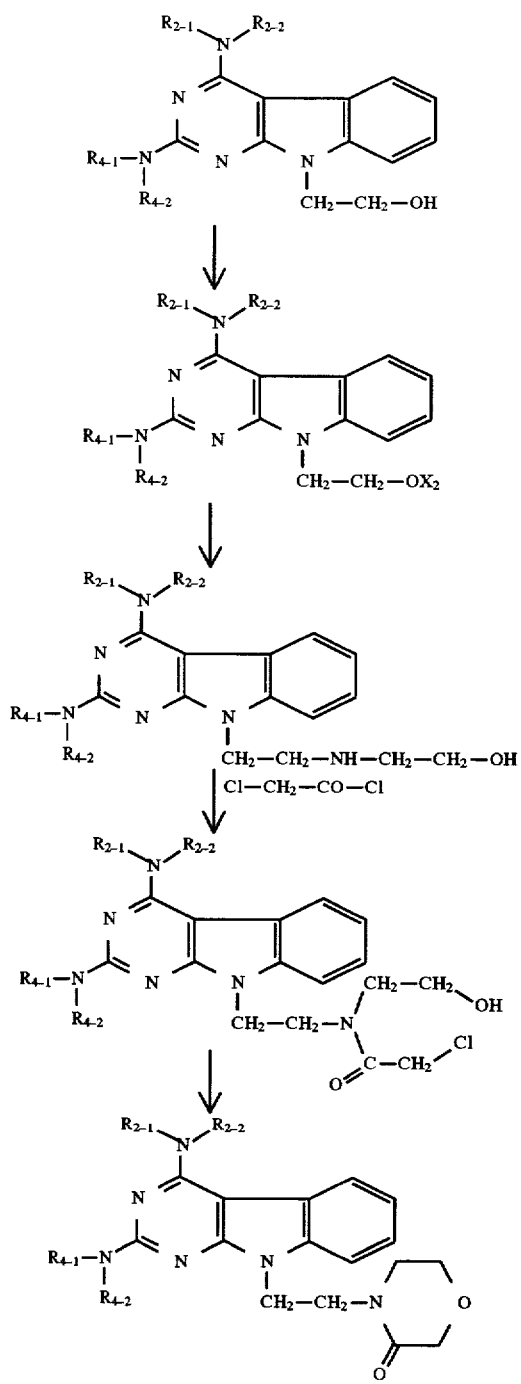

We claim:
1. Pyrimido[4,5-b]indoles of the formula (I)

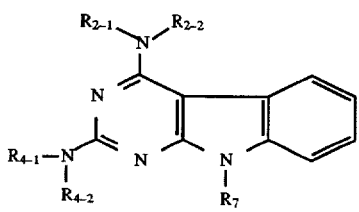

where $R_{2-1}$ is (A) —H,
(B) $C_1$–$C_8$ alkyl optionally substituted with 1 thru 4
  (1) —$OR_{2-10}$ where $R_{2-10}$ is
    (a) —H,
    (b) $C_1$–$C_4$ alkyl,
    (c) —CO—$R_{2-11}$ where $R_{2-11}$ is $C_1$–$C_4$ alkyl or $C_6$–$C_9$ aralkyl,
    (d) —CO—$NR_{2-12}R_{2-13}$ where $R_{2-12}$ and $R_{2-13}$ are the same or different and are —H or $C_1$–$C_2$ alkyl,
where $R_{2-2}$ is
(A) —H,
(B) $C_1$–$C_8$ alkyl optionally substituted with 1 thru 4
  (1) —$OR_{2-10}$ where $R_{2-10}$ is as defined above, or $R_{2-1}$ and $R_{2-2}$ are taken together with the attached nitrogen atom to form a heterocyclic ring selected from the group consisting of 1-pyrrolidinyl, 1-piperdinyl4-morpholinyl, 4-methylpiperazinyl, 4-thiomorpholinyl and 1-piperazinyl,
where $R_{4-1}$ is defined the same as $R_{2-1}$, but may be the same or different than $R_{2-1}$,
where $R_{4-2}$ is defined the same as $R_{2-2}$ but may be the same or different than $R_{2-2}$;
where $R_7$ is
(A) $C_1$–$C_8$ alkyl substituted with 1 thru 4 $R_{7-1}$ where $R_{7-1}$ is
  (1) —$OR_{7-2}$ where $R_{7-2}$ is
    (a) —H,
    (b) $C_1$–$C_4$ alkyl,
    (c) —CO—$R_{7-8}$ where $R_{7-8}$ is $C_1$–$C_4$ alkyl or $C_8$–$C_9$ aralkyl,
    (d) —CO—$NR_{7-10}R_{7-11}$ where $R_{7-10}$ and $R_{7-11}$ are the same or different and are —H or $C_1$–$C_3$ alkyl,
  (2) —$NR_{7-4}R_{7-5}$ where $R_{7-4}$ and $R_{7-6}$ are the same or different and are $C_1$–$C_4$ alkyl or may taken together with the attached nitrogen atom to form the heterocyclic ring —N*—(CH$_2$)$_{n1}$—R$_{5-6}$—(CH$_2$)$_{n2}$* where the atoms marked with an asterisk (*) are bonded together resulting in the formation of a ring, where $n_1$ is 1 thru 5, $n_2$ is 0 thru 3 and $R_{5-6}$ is
    (a) —$C_2$—,
    (b) —O—,
    (c) —S—,
  (3) —(CH$_2$)$_{n3}$CO$_2$R$_{7-2}$, where $n_3$ is 0 thru 6 and $R_{7-2}$ is as defined above,
  (4) —(CH$_2$)$_{n3}$CON(R$_{7-3}$)$_3$ where $n_3$ is as defined as above and where $R_{7-3}$ may be the same or different and is —H or $C_1$–$C_3$ alkyl,
  (5) —(CH$_2$)$_{n3}$CONR$_{7-4}$R$_{7-5}$ where $n_3$, $R_{7-4}$, $R_{7-5}$ are as defined above,
  (6) —(CH$_2$)$_{n1}$OR$_{7-2}$ where $R_{7-2}$ and $n_1$ are as defined above,
  (7) —(CH$_2$)$_{n2}$OCOR$_{7-3}$ where $R_{7-3}$ and $n_1$ are as defined above, and pharmaceutically acceptable salts thereof.

2. Pyrimido[4,5-b]indoles (I) according to claim 1 where $R_{2-1}$ and $R_{2-2}$ are taken together with the attached nitrogen atom to form 1-pyrrolidinyl, 1-piperidinyl, 4-morpholinyl, 4-methylpiperazinyl, 4-thiomorpholinyl and 1-piperazinyl.

3. Pyrimido[4,5-b]indoles (I) according to claim 2 where $R_{2-1}$ and $R_{2-2}$ are 1-pyrrolidinyl and 1-piperazinyl.

4. Pyrimido[4,5-b]indoles (I) according to claim 2 where $R_{4-1}$ and $R_{4-2}$ are taken together with the attached nitrogen atom to form 1-pyrrolidinyl, 1-piperidinyl, 4-30 morpholinyl, 4-methylpiperazinyl, 4-thiomorpholinyl and 1-piperazinyl.

5. Pyrimido[4,5-b]indoles (I) according to claim 4 where $R_{4-1}$ and $R_{4-2}$ are 1-pyrrolidinyl and 1-piperazinyl.

6. Pyrimido[4,5-b]indoles (I) according to claim 2 where $R_7$ is 2-(4-morpholinyl)ethyl, and 2-(1-piperidinyl)ethyl.

7. Pyrimido[4,5-b]indoles (I) according to claim 6 where $R_7$ is 2-(4-morpholinyl)ethyl.

8. Pyrimido[4,5-b]indoles (I) according to claim 2 where the pharmaceutically acceptable salts are salts of the following acids hydrochloric, hydrobromic, methanesulfonic, sulfuric, phosphoric, nitric, benzoic, citric, tartaric, fumaric, maleic, $CH_3-(CH_2)_n-COOH$ where n is 0 thru 4, $HOOC-(CH_2)n-COOH$ where n is as defined above.

9. Pyrimido[4,5-b]indoles (I) according to claim 2 where the pyrimido[4,5-b]indole is selected from the group consisting of 9-(2-hydroxyethyl)-2,4-di-1-pyrrolidinyl-9H-pyrimido[4,5-b]indole, 9-[2-(1-piperidinyl)ethyl]-2,4-di-1-pyrrolidinyl-9H-pyrimido[4,5-b]indole, 9-[2-(4-morpholinyl)ethyl]-2,4-di-1-pyrrolidinyl-9H-pyrimido[4,5-b]indole.

10. Pyrimido[4,5-b]indoles (I) according to claim 9 where the pyrimido[4,5-b]indole is 9-[2-(4-morpholinyl)ethyl]-2,4-di-1-pyrrolidinyl-9H-pyrimido[4,5-b]indole.

11. Pyrimido[4,5-b]indoles (I) according to claim 10 where the pyrimido[4,5-b]indole is:

9-[2-(4-morpholinyl)ethyl]-2,4-di-1-pyrrolidinyl-9H-pyrimido[4,5-b]indole monohydrochloride, 9-[2-(4-morpholinyl)ethyl]-2,4-di-1-pyrrolidinyl-9H-pyrimido[4,5-b]indole sulfate.

12. Pyrimido[4,5-b]indoles (I) according to claim 11 where the pyrimido[4,5-b]indole is 9-[2-(4-morpholinyl)ethyl]-2,4-di-1-pyrrolidinyl-9H-pyrimido[4,5-b]indole monohydrochloride.

* * * * *